(12) United States Patent
Caban et al.

(10) Patent No.: US 11,672,982 B2
(45) Date of Patent: Jun. 13, 2023

(54) CONTROL SYSTEM FOR MOVEMENT RECONSTRUCTION AND/OR RESTORATION FOR A PATIENT

(71) Applicant: ONWARD MEDICAL N.V., Eindhoven (NL)

(72) Inventors: Miroslav Caban, Eindhoven (NL); Niek Borgers, Eindhoven (NL); Urs Keller, Eindhoven (NL); Joachim von Zitzewitz, Eindhoven (NL); Jurriaan Bakker, Eindhoven (NL); Vincent Delattre, Eindhoven (NL); Hans Pflug, Eindhoven (NL); Maryse van't Klooster, Eindhoven (NL); Andre Kleibeuker, Eindhoven (NL)

(73) Assignee: Onward Medical N.V., Eindhoven (NL)

( * ) Notice: Subject to any disclaimer, the term of this patent is extended or adjusted under 35 U.S.C. 154(b) by 610 days.

(21) Appl. No.: 16/682,833

(22) Filed: Nov. 13, 2019

(65) Prior Publication Data
US 2020/0147382 A1    May 14, 2020

(30) Foreign Application Priority Data
Nov. 13, 2018    (EP) .................................... 18205821

(51) Int. Cl.
*A61N 1/36*        (2006.01)
*A61H 3/00*        (2006.01)
(Continued)

(52) U.S. Cl.
CPC .......... *A61N 1/36031* (2017.08); *A61H 3/00* (2013.01); *A61H 3/008* (2013.01);
(Continued)

(58) Field of Classification Search
CPC ............ A61N 1/36031; A61N 1/36003; A61N 1/36017; A61N 1/3603; A61N 1/36135
See application file for complete search history.

(56) References Cited

U.S. PATENT DOCUMENTS 2,868,343 A    1/1959    Sproul
3,543,761 A    12/1970   Bradley
(Continued)

FOREIGN PATENT DOCUMENTS

AU    2012204526      9/2016
CA    2856202 A1     5/2013
(Continued)

OTHER PUBLICATIONS

Bizzi, E. et al., "Modular Organization of Motor Behavior," Trends in Neurosciences, vol. 18, No. 10, Oct. 1995, 8 pages.
(Continued)

*Primary Examiner* — Amanda K Hulbert
*Assistant Examiner* — Philip C Edwards
(74) *Attorney, Agent, or Firm* — Finnegan, Henderson, Farabow, Garrett & Dunner, LLP

(57) ABSTRACT

A control system for a movement reconstruction and/or restoration system for a patient, comprising
  at least one sensor,
  at least one controller,
  at least one programmer,
  at least one stimulation system,
wherein the controller is connected with the sensor, the programmer and the stimulation system,
wherein the sensor is part of or attached to a training entity in order to
  create and/or guide a movement model for a patient and/or
  adjust stimulation settings based on sensor input.

20 Claims, 17 Drawing Sheets

(51) Int. Cl.
*A63B 22/02* (2006.01)
*A63B 22/06* (2006.01)

(52) U.S. Cl.
CPC ....... *A61N 1/36003* (2013.01); *A61N 1/3603* (2017.08); *A61N 1/36017* (2013.01); *A61N 1/36062* (2017.08); *A61N 1/36135* (2013.01); *A61N 1/36139* (2013.01); *A63B 22/02* (2013.01); *A63B 22/06* (2013.01); *A61H 2201/10* (2013.01); *A61H 2201/165* (2013.01); *A61H 2230/625* (2013.01); *A61N 1/36067* (2013.01)

(56) References Cited

U.S. PATENT DOCUMENTS

| | | |
|---|---|---|
| 3,650,277 A | 3/1972 | Sjostrand et al. |
| 3,662,758 A | 5/1972 | Glover |
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,398,537 A | 8/1983 | Holmbo |
| 4,414,986 A | 11/1983 | Dickhudt et al. |
| 4,538,624 A | 9/1985 | Tarjan |
| 4,549,556 A | 10/1985 | Tarjan et al. |
| 4,559,948 A | 12/1985 | Liss et al. |
| 4,569,352 A | 2/1986 | Petrofsky et al. |
| 4,573,481 A | 3/1986 | Bullara |
| 4,724,842 A | 2/1988 | Charters |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,018,631 A | 5/1991 | Reimer |
| 5,031,618 A | 7/1991 | Mullet |
| 5,066,272 A | 11/1991 | Eaton et al. |
| 5,081,989 A | 1/1992 | Graupe et al. |
| 5,121,754 A | 6/1992 | Mullett |
| 5,344,439 A | 9/1994 | Otten |
| 5,354,320 A | 10/1994 | Schaldach et al. |
| 5,366,813 A | 11/1994 | Berlin |
| 5,374,285 A | 12/1994 | Vaiani et al. |
| 5,417,719 A | 5/1995 | Hull et al. |
| 5,476,441 A | 12/1995 | Durfee et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,058,331 A | 5/2000 | King |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,463,327 B1 | 10/2002 | Lurie et al. |
| 6,470,213 B1 | 10/2002 | Alley |
| 6,500,110 B1 | 12/2002 | Davey et al. |
| 6,503,231 B1 | 1/2003 | Prausnitz et al. |
| 6,505,074 B2 | 1/2003 | Boveja et al. |
| 6,516,227 B1 | 2/2003 | Meadows et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,748,276 B1 | 6/2004 | Daignault, Jr. et al. |
| 6,819,956 B2 | 11/2004 | DiLorenzo |
| 6,839,594 B2 | 1/2005 | Cohen et al. |
| 6,862,479 B1 | 3/2005 | Whitehurst et al. |
| 6,871,099 B1 | 3/2005 | Whitehurst et al. |
| 6,878,112 B2 | 4/2005 | Linberg et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,125,388 B1 | 10/2006 | Reinkensmeyer et al. |
| 7,127,287 B2 | 10/2006 | Duncan et al. |
| 7,127,296 B2 | 10/2006 | Bradley |
| 7,127,297 B2 | 10/2006 | Law et al. |
| 7,149,773 B2 | 12/2006 | Haller et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Van Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel |
| 7,324,853 B2 | 1/2008 | Ayal et al. |
| 7,330,760 B2 | 2/2008 | Heruth et al. |
| 7,337,005 B2 | 2/2008 | Kim et al. |
| 7,337,006 B2 | 2/2008 | Kim et al. |
| 7,381,192 B2 | 6/2008 | Brodard et al. |
| 7,415,309 B2 | 8/2008 | McIntyre |
| 7,463,927 B1 | 12/2008 | Chaouat |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| 7,544,185 B2 | 6/2009 | Bengtsson |
| 7,584,000 B2 | 9/2009 | Erickson |
| 7,590,454 B2 | 9/2009 | Garabedian et al. |
| 7,603,178 B2 | 10/2009 | North et al. |
| 7,620,502 B2 | 11/2009 | Selifonov et al. |
| 7,628,750 B2 | 12/2009 | Cohen et al. |
| 7,647,115 B2 | 1/2010 | Levin et al. |
| 7,660,636 B2 | 2/2010 | Castel et al. |
| 7,697,995 B2 | 4/2010 | Cross, Jr. et al. |
| 7,725,193 B1 | 5/2010 | Chu |
| 7,729,781 B2 | 6/2010 | Swoyer et al. |
| 7,734,340 B2 | 6/2010 | de Ridder |
| 7,734,351 B2 | 6/2010 | Testerman et al. |
| 7,742,037 B2 | 6/2010 | Sako et al. |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,813,809 B2 | 10/2010 | Strother et al. |
| 7,856,264 B2 | 12/2010 | Firlik et al. |
| 7,877,146 B2 | 1/2011 | Rezai et al. |
| 7,890,182 B2 | 2/2011 | Parramon et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,051 B2 | 1/2012 | Cross, Jr. et al. |
| 8,108,052 B2 | 1/2012 | Boling |
| 8,131,358 B2 | 3/2012 | Moffitt et al. |
| 8,135,473 B2 | 3/2012 | Miesel et al. |
| 8,155,750 B2 | 4/2012 | Jaax et al. |
| 8,168,481 B2 | 5/2012 | Hanaoka et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |

(56) References Cited

U.S. PATENT DOCUMENTS

| | | |
|---|---|---|
| 8,214,048 B1 | 7/2012 | Whitehurst et al. |
| 8,229,565 B2 | 7/2012 | Kim et al. |
| 8,239,038 B2 | 8/2012 | Wolf, II |
| 8,260,436 B2 | 9/2012 | Gerber et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,326,569 B2 | 12/2012 | Lee et al. |
| 8,332,029 B2 | 12/2012 | Glukhovsky et al. |
| 8,332,047 B2 | 12/2012 | Libbus et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | de Ridder |
| 8,369,961 B2 | 2/2013 | Christman et al. |
| 8,374,696 B2 | 2/2013 | Sanchez et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| 8,543,200 B2 | 9/2013 | Lane et al. |
| 8,588,884 B2 | 11/2013 | Hegde et al. |
| 8,626,300 B2 | 1/2014 | Demarais et al. |
| 8,700,145 B2 | 4/2014 | Kilgard et al. |
| 8,712,546 B2 | 4/2014 | Kim et al. |
| 8,740,825 B2 | 6/2014 | Ehrenreich et al. |
| 8,750,957 B2 | 6/2014 | Tang et al. |
| 8,768,481 B2 | 7/2014 | Lane |
| 8,805,542 B2 | 8/2014 | Tai et al. |
| 9,072,891 B1 | 7/2015 | Rao |
| 9,079,039 B2 | 7/2015 | Carlson et al. |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,248,291 B2 | 2/2016 | Mashiach |
| 9,272,139 B2 | 3/2016 | Hamilton et al. |
| 9,272,143 B2 | 3/2016 | Libbus et al. |
| 9,283,391 B2 | 3/2016 | Ahmed |
| 9,314,630 B2 | 4/2016 | Levin et al. |
| 9,393,409 B2 | 7/2016 | Edgerton et al. |
| 9,409,023 B2 | 8/2016 | Burdick et al. |
| 9,415,218 B2 | 8/2016 | Edgerton et al. |
| 9,421,365 B2 | 8/2016 | Sumners et al. |
| 9,597,517 B2 | 3/2017 | Moffitt |
| 9,610,442 B2 | 4/2017 | Yoo et al. |
| 9,802,052 B2 | 10/2017 | Marnfeldt |
| 9,895,545 B2 | 2/2018 | Rao et al. |
| 9,993,642 B2 | 6/2018 | Gerasimenko et al. |
| 10,092,750 B2 | 10/2018 | Edgerton et al. |
| 10,124,166 B2 | 11/2018 | Edgerton et al. |
| 10,137,299 B2 | 11/2018 | Lu et al. |
| 10,406,366 B2 | 9/2019 | Westlund et al. |
| 10,449,371 B2 | 10/2019 | Serrano Carmona |
| 10,751,533 B2 | 8/2020 | Edgerton et al. |
| 10,773,074 B2 | 9/2020 | Liu et al. |
| 10,806,927 B2 | 10/2020 | Edgerton et al. |
| 10,806,935 B2 | 10/2020 | Rao et al. |
| 11,097,122 B2 | 8/2021 | Lu |
| 11,123,312 B2 | 9/2021 | Lu et al. |
| 2001/0016266 A1 | 8/2001 | Okazaki et al. |
| 2001/0032992 A1 | 10/2001 | Wendt |
| 2002/0042814 A1 | 4/2002 | Fukasawa et al. |
| 2002/0052539 A1 | 5/2002 | Haller et al. |
| 2002/0055779 A1 | 5/2002 | Andrews |
| 2002/0083240 A1 | 6/2002 | Hoese et al. |
| 2002/0111661 A1 | 8/2002 | Cross et al. |
| 2002/0115945 A1 | 8/2002 | Herman et al. |
| 2002/0187260 A1 | 12/2002 | Sheppard, Jr. et al. |
| 2002/0188332 A1 | 12/2002 | Lurie et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0093021 A1 | 5/2003 | Goffer |
| 2003/0100933 A1 | 5/2003 | Ayal et al. |
| 2003/0114894 A1 | 6/2003 | Dar et al. |
| 2003/0158583 A1 | 8/2003 | Burnett et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0111126 A1 | 6/2004 | Tanagho et al. |
| 2004/0122483 A1 | 6/2004 | Nathan et al. |
| 2004/0127954 A1 | 7/2004 | McDonald, III |
| 2004/0133248 A1 | 7/2004 | Frei et al. |
| 2004/0138518 A1 | 7/2004 | Rise et al. |
| 2004/0172027 A1 | 9/2004 | Speitling et al. |
| 2004/0172097 A1 | 9/2004 | Brodard et al. |
| 2004/0181263 A1 | 9/2004 | Balzer et al. |
| 2004/0267320 A1 | 12/2004 | Taylor et al. |
| 2005/0004622 A1 | 1/2005 | Cullen et al. |
| 2005/0061315 A1 | 3/2005 | Lee et al. |
| 2005/0070982 A1 | 3/2005 | Heruth et al. |
| 2005/0075662 A1 | 4/2005 | Pedersen et al. |
| 2005/0075669 A1 | 4/2005 | King |
| 2005/0075678 A1 | 4/2005 | Faul |
| 2005/0090756 A1 | 4/2005 | Wolf et al. |
| 2005/0101827 A1 | 5/2005 | Delisle |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0231186 A1 | 10/2005 | Saavedra Barrera et al. |
| 2005/0246004 A1 | 11/2005 | Cameron et al. |
| 2005/0277999 A1 | 12/2005 | Strother et al. |
| 2005/0278000 A1 | 12/2005 | Strother et al. |
| 2006/0003090 A1 | 1/2006 | Rodger et al. |
| 2006/0015153 A1 | 1/2006 | Gliner et al. |
| 2006/0018360 A1 | 1/2006 | Tai et al. |
| 2006/0041225 A1 | 2/2006 | Wallace et al. |
| 2006/0041295 A1 | 2/2006 | Osypka |
| 2006/0089696 A1 | 4/2006 | Olsen et al. |
| 2006/0100671 A1 | 5/2006 | De Ridder |
| 2006/0111754 A1 | 5/2006 | Rezai et al. |
| 2006/0122678 A1 | 6/2006 | Olsen et al. |
| 2006/0142337 A1 | 6/2006 | Ikeura et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189839 A1 | 8/2006 | Laniado et al. |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2006/0282127 A1 | 12/2006 | Zealear |
| 2007/0004567 A1 | 1/2007 | Shetty et al. |
| 2007/0016097 A1 | 1/2007 | Farquhar et al. |
| 2007/0016266 A1 | 1/2007 | Paul, Jr. |
| 2007/0016329 A1 | 1/2007 | Herr et al. |
| 2007/0021513 A1 | 1/2007 | Agee et al. |
| 2007/0027495 A1 | 2/2007 | Gerber |
| 2007/0047852 A1 | 3/2007 | Sharp et al. |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0067003 A1 | 3/2007 | Sanchez et al. |
| 2007/0073357 A1 | 3/2007 | Rooney et al. |
| 2007/0083240 A1 | 4/2007 | Peterson et al. |
| 2007/0100389 A1 | 5/2007 | Jaax et al. |
| 2007/0121702 A1 | 5/2007 | LaGuardia et al. |
| 2007/0121709 A1 | 5/2007 | Ittogi |
| 2007/0142874 A1 | 6/2007 | John |
| 2007/0150023 A1 | 6/2007 | Ignagni et al. |
| 2007/0156172 A1 | 7/2007 | Alvarado |
| 2007/0156179 A1 | 7/2007 | S.E. |
| 2007/0156200 A1 | 7/2007 | Kornet et al. |
| 2007/0168008 A1 | 7/2007 | Olsen |
| 2007/0179534 A1 | 8/2007 | Firlik et al. |
| 2007/0179579 A1 | 8/2007 | Feler et al. |
| 2007/0191709 A1 | 8/2007 | Swanson |

(56) References Cited

U.S. PATENT DOCUMENTS

| | | |
|---|---|---|
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265621 A1 | 11/2007 | Matthis et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2007/0029391 A1 | 12/2007 | Strother et al. |
| 2008/0002227 A1 | 1/2008 | Tsujimoto |
| 2008/0004674 A1 | 1/2008 | King et al. |
| 2008/0009927 A1 | 1/2008 | Vilims |
| 2008/0021513 A1 | 1/2008 | Thacker et al. |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0077192 A1 | 3/2008 | Harry et al. |
| 2008/0103579 A1 | 5/2008 | Gerber |
| 2008/0105185 A1 | 5/2008 | Kuhlman |
| 2008/0140152 A1 | 6/2008 | Imran et al. |
| 2008/0140162 A1 | 6/2008 | Goetz et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2009/0012436 A1 | 1/2009 | Lanfermann et al. |
| 2009/0024997 A1 | 1/2009 | Kobayashi |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0131995 A1 | 5/2009 | Sloan et al. |
| 2009/0157141 A1 | 6/2009 | Chiao et al. |
| 2009/0198305 A1 | 8/2009 | Naroditsky et al. |
| 2009/0229166 A1 | 9/2009 | Sawrie |
| 2009/0204173 A1 | 10/2009 | Zhao et al. |
| 2009/0270960 A1 | 10/2009 | Zhao et al. |
| 2009/0281529 A1 | 11/2009 | Carriazo |
| 2009/0281599 A1 | 11/2009 | Thacker et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0010646 A1 | 1/2010 | Drew et al. |
| 2010/0023103 A1 | 1/2010 | Elborno |
| 2010/0029040 A1 | 2/2010 | Nomoto |
| 2010/0042193 A1 | 2/2010 | Slavin |
| 2010/0070007 A1 | 3/2010 | Parker et al. |
| 2010/0114205 A1 | 5/2010 | Donofrio et al. |
| 2010/0114239 A1 | 5/2010 | McDonald, III |
| 2010/0125313 A1 | 5/2010 | Lee et al. |
| 2010/0137238 A1 | 6/2010 | Gan et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0166546 A1 | 7/2010 | Mahan et al. |
| 2010/0168820 A1 | 7/2010 | Maniak et al. |
| 2010/0185253 A1 | 7/2010 | Dimarco et al. |
| 2010/0198298 A1 | 8/2010 | Glukhovsky et al. |
| 2010/0217355 A1 | 8/2010 | Tass et al. |
| 2010/0022831 A1 | 9/2010 | Shuros et al. |
| 2010/0241121 A1 | 9/2010 | Logan et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0280570 A1 | 11/2010 | Sturm et al. |
| 2010/0305660 A1 | 12/2010 | Hegi et al. |
| 2010/0312304 A1 | 12/2010 | York et al. |
| 2010/0318168 A1 | 12/2010 | Bighetti |
| 2010/0331925 A1 | 12/2010 | Peterson |
| 2011/0006793 A1 | 1/2011 | Peschke et al. |
| 2011/0009919 A1 | 1/2011 | Carbunaru et al. |
| 2011/0016081 A1 | 1/2011 | Basak et al. |
| 2011/0029040 A1 | 2/2011 | Walker et al. |
| 2011/0029044 A1 | 2/2011 | Hyde et al. |
| 2011/0034277 A1 | 2/2011 | Brandes |
| 2011/0034977 A1 | 2/2011 | Janik et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054570 A1 | 3/2011 | Lane |
| 2011/0054579 A1 | 3/2011 | Kumar et al. |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184482 A1 | 7/2011 | Eberman et al. |
| 2011/0184488 A1 | 7/2011 | De Ridder |
| 2011/0184489 A1 | 7/2011 | Nicolelis et al. |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | DeGiorgio et al. |
| 2011/0218594 A1 | 9/2011 | Doron et al. |
| 2011/0224153 A1 | 9/2011 | Levitt et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224757 A1 | 9/2011 | Zdeblick et al. |
| 2011/0230101 A1 | 9/2011 | Tang et al. |
| 2011/0230701 A1 | 9/2011 | Simon et al. |
| 2011/0230702 A1 | 9/2011 | Honour |
| 2011/0231326 A1 | 9/2011 | Marino |
| 2011/0237221 A1 | 9/2011 | Prakash et al. |
| 2011/0237921 A1 | 9/2011 | Askin, III et al. |
| 2011/0245734 A1 | 10/2011 | Wagner et al. |
| 2011/0276107 A1 | 11/2011 | Simon et al. |
| 2011/0288609 A1 | 11/2011 | Tehrani et al. |
| 2011/0295100 A1 | 12/2011 | Hegde et al. |
| 2012/0006793 A1 | 1/2012 | Swanson |
| 2012/0011950 A1 | 1/2012 | Kracke |
| 2012/0013041 A1 | 1/2012 | Cao et al. |
| 2012/0013126 A1 | 1/2012 | Molloy |
| 2012/0016448 A1 | 1/2012 | Lee |
| 2012/0029528 A1 | 2/2012 | MacDonald et al. |
| 2012/0035684 A1 | 2/2012 | Thompson et al. |
| 2012/0041518 A1 | 2/2012 | Kim et al. |
| 2012/0052432 A1 | 3/2012 | Matsuura |
| 2012/0059432 A1 | 3/2012 | Emborg et al. |
| 2012/0071250 A1 | 3/2012 | O'Neil et al. |
| 2012/0071950 A1 | 3/2012 | Archer |
| 2012/0083709 A1 | 4/2012 | Parker et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0116476 A1 | 5/2012 | Kothandaraman |
| 2012/0123223 A1 | 5/2012 | Freeman et al. |
| 2012/0123293 A1 | 5/2012 | Shah et al. |
| 2012/0126392 A1 | 5/2012 | Kalvesten et al. |
| 2012/0136408 A1 | 5/2012 | Grill et al. |
| 2012/0165899 A1 | 6/2012 | Gliner |
| 2012/0172222 A1 | 7/2012 | Artigas Puerto |
| 2012/0172246 A1 | 7/2012 | Nguyen et al. |
| 2012/0172946 A1 | 7/2012 | Alataris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0203055 A1 | 8/2012 | Pletnev |
| 2012/0203131 A1 | 8/2012 | DiLorenzo |
| 2012/0221073 A1 | 8/2012 | Southwell et al. |
| 2012/0232615 A1 | 9/2012 | Barolat et al. |
| 2012/0252380 A1 | 10/2012 | Kawakita |
| 2012/0252874 A1 | 10/2012 | Feinstein et al. |
| 2012/0259380 A1 | 10/2012 | Pyles |
| 2012/0271372 A1 | 10/2012 | Osario |
| 2012/0277824 A1 | 11/2012 | Li |
| 2012/0277834 A1 | 11/2012 | Mercanzini et al. |

(56) References Cited

U.S. PATENT DOCUMENTS

| | | |
|---|---|---|
| 2012/0283697 A1 | 11/2012 | Kim et al. |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330321 A1 | 12/2012 | Johnson et al. |
| 2012/0330391 A1 | 12/2012 | Bradley et al. |
| 2013/0012853 A1 | 1/2013 | Brown |
| 2013/0013041 A1 | 1/2013 | Glukhovsky et al. |
| 2013/0026640 A1 | 1/2013 | Ito et al. |
| 2013/0030312 A1 | 1/2013 | Keel et al. |
| 2013/0030319 A1 | 1/2013 | Hettrick et al. |
| 2013/0030501 A1 | 1/2013 | Feler et al. |
| 2013/0035745 A1 | 2/2013 | Ahmed et al. |
| 2013/0053922 A1 | 2/2013 | Ahmed et al. |
| 2013/0066392 A1 | 3/2013 | Simon et al. |
| 2013/0085317 A1 | 4/2013 | Feinstein |
| 2013/0085361 A1 | 4/2013 | Mercanzini et al. |
| 2013/0096640 A1 | 4/2013 | Possover |
| 2013/0096661 A1 | 4/2013 | Greenberg et al. |
| 2013/0096662 A1 | 4/2013 | Swanson |
| 2013/0110196 A1 | 5/2013 | Alataris et al. |
| 2013/0116751 A1 | 5/2013 | Moffitt et al. |
| 2013/0123568 A1 | 5/2013 | Hamilton et al. |
| 2013/0123659 A1 | 5/2013 | Bartol et al. |
| 2013/0138167 A1 | 5/2013 | Bradley et al. |
| 2013/0165991 A1 | 6/2013 | Kim et al. |
| 2013/0197408 A1 | 8/2013 | Goldfarb et al. |
| 2013/0204324 A1 | 8/2013 | Thacker et al. |
| 2013/0211477 A1 | 8/2013 | Cullen et al. |
| 2013/0237948 A1 | 9/2013 | Donders et al. |
| 2013/0253222 A1 | 9/2013 | Nakao |
| 2013/0253229 A1 | 9/2013 | Sawant et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0289446 A1 | 10/2013 | Stone et al. |
| 2013/0289650 A1 | 10/2013 | Karlsson et al. |
| 2013/0289664 A1 | 10/2013 | Johanek |
| 2013/0289667 A1 | 10/2013 | Wacnik et al. |
| 2013/0296965 A1 | 11/2013 | Mokelke et al. |
| 2013/0303873 A1 | 11/2013 | Voros et al. |
| 2013/0304159 A1 | 11/2013 | Simon et al. |
| 2013/0310211 A1 | 11/2013 | Wilton et al. |
| 2013/0310911 A1 | 11/2013 | Tai et al. |
| 2014/0005753 A1 | 1/2014 | Carbunaru |
| 2014/0058292 A1 | 2/2014 | Alford et al. |
| 2014/0058490 A1 | 2/2014 | DiMarco |
| 2014/0066950 A1 | 3/2014 | MacDonald et al. |
| 2014/0067007 A1 | 3/2014 | Drees et al. |
| 2014/0067354 A1 | 3/2014 | Kaula et al. |
| 2014/0074190 A1 | 3/2014 | Griffith |
| 2014/0081011 A1 | 3/2014 | Vaught et al. |
| 2014/0081071 A1 | 3/2014 | Simon et al. |
| 2014/0088674 A1 | 3/2014 | Bradley |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0163640 A1 | 6/2014 | Edgerton et al. |
| 2014/0172045 A1 | 6/2014 | Yip et al. |
| 2014/0180361 A1 | 6/2014 | Burdick et al. |
| 2014/0213842 A1 | 7/2014 | Simon et al. |
| 2014/0228905 A1 | 8/2014 | Bolea |
| 2014/0236257 A1 | 8/2014 | Parker et al. |
| 2014/0243923 A1 | 8/2014 | Doan et al. |
| 2014/0277271 A1 | 9/2014 | Chan et al. |
| 2014/0296752 A1 | 10/2014 | Edgerton et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1 | 11/2014 | Rocon de Lima et al. |
| 2014/0357936 A1 | 12/2014 | Simon et al. |
| 2015/0005840 A1 | 1/2015 | Pal et al. |
| 2015/0065559 A1 | 3/2015 | Feinstein et al. |
| 2015/0066111 A1 | 3/2015 | Blum et al. |
| 2015/0165226 A1 | 6/2015 | Simon et al. |
| 2015/0182784 A1 | 7/2015 | Barriskill et al. |
| 2015/0190634 A1 | 7/2015 | Rezai et al. |
| 2015/0196231 A1 | 7/2015 | Ziaie et al. |
| 2015/0217120 A1 | 8/2015 | Nandra et al. |
| 2015/0231396 A1 | 8/2015 | Burdick et al. |
| 2015/0265830 A1 | 9/2015 | Simon et al. |
| 2015/0328462 A1 | 11/2015 | Griffith |
| 2016/0001096 A1 | 1/2016 | Mishelevich |
| 2016/0030737 A1 | 2/2016 | Gerasimenko et al. |
| 2016/0030748 A1 | 2/2016 | Edgerton et al. |
| 2016/0030750 A1 | 2/2016 | Bokil et al. |
| 2016/0045727 A1 | 2/2016 | Rezai et al. |
| 2016/0045731 A1 | 2/2016 | Simon et al. |
| 2016/0074663 A1 | 3/2016 | De Ridder |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0121121 A1 | 5/2016 | Mashiach |
| 2016/0143588 A1 | 5/2016 | Hoitink et al. |
| 2016/0157389 A1 | 6/2016 | Hwang |
| 2016/0175586 A1 | 6/2016 | Edgerton et al. |
| 2016/0220813 A1 | 8/2016 | Edgerton et al. |
| 2016/0235977 A1 | 8/2016 | Lu et al. |
| 2016/0310739 A1 | 10/2016 | Burdick et al. |
| 2017/0007320 A1 | 1/2017 | Levin et al. |
| 2017/0007831 A1 | 1/2017 | Edgerton et al. |
| 2017/0128729 A1 | 5/2017 | Netoff et al. |
| 2017/0157389 A1 | 6/2017 | Tai et al. |
| 2017/0157396 A1 | 6/2017 | Dixon et al. |
| 2017/0161454 A1 | 6/2017 | Grill et al. |
| 2017/0165497 A1 | 6/2017 | Lu |
| 2017/0173326 A1 | 6/2017 | Bloch et al. |
| 2017/0246450 A1 | 8/2017 | Liu et al. |
| 2017/0246452 A1 | 8/2017 | Liu et al. |
| 2017/0266455 A1 | 9/2017 | Steinke |
| 2017/0274209 A1 | 9/2017 | Edgerton et al. |
| 2017/0296837 A1 | 10/2017 | Jin |
| 2017/0354819 A1 | 12/2017 | Bloch et al. |
| 2017/0361093 A1* | 12/2017 | Yoo ................. A61N 1/36107 |
| 2018/0056078 A1 | 3/2018 | Kashyap et al. |
| 2018/0085583 A1 | 3/2018 | Zhang et al. |
| 2018/0104479 A1 | 4/2018 | Grill et al. |
| 2018/0110992 A1 | 4/2018 | Parramon et al. |
| 2018/0125810 A1 | 5/2018 | Schwarz et al. |
| 2018/0178008 A1* | 6/2018 | Bouton ................. A61F 2/72 |
| 2018/0185642 A1 | 7/2018 | Lu |
| 2018/0185648 A1 | 7/2018 | Nandra et al. |
| 2018/0193655 A1 | 7/2018 | Zhang et al. |
| 2018/0229037 A1 | 8/2018 | Edgerton et al. |
| 2018/0229038 A1 | 8/2018 | Burdick et al. |
| 2018/0236240 A1 | 8/2018 | Harkema et al. |
| 2018/0256906 A1 | 9/2018 | Pivonka et al. |
| 2018/0280693 A1 | 10/2018 | Edgerton et al. |
| 2018/0353755 A1 | 12/2018 | Edgerton et al. |
| 2018/0361146 A1 | 12/2018 | Gerasimenko et al. |
| 2019/0022371 A1 | 1/2019 | Chang et al. |
| 2019/0033622 A1 | 1/2019 | Olgun et al. |
| 2019/0160294 A1 | 5/2019 | Peterson et al. |
| 2019/0167987 A1 | 6/2019 | Lu et al. |
| 2019/0192864 A1 | 6/2019 | Koop et al. |
| 2019/0247650 A1* | 8/2019 | Tran ................. A61N 1/3704 |
| 2019/0269917 A1 | 9/2019 | Courtine et al. |
| 2019/0381313 A1 | 12/2019 | Lu |
| 2019/0381328 A1 | 12/2019 | Wechter et al. |
| 2020/0155865 A1 | 5/2020 | Lu |
| 2020/0228901 A1 | 7/2020 | Baek |
| 2021/0069052 A1 | 3/2021 | Burke |
| 2021/0187278 A1 | 6/2021 | Lu |

(56) References Cited

U.S. PATENT DOCUMENTS

| | | |
|---|---|---|
| 2021/0236837 A1 | 8/2021 | Lu |
| 2021/0378991 A1 | 12/2021 | Lu |

FOREIGN PATENT DOCUMENTS

| | | | |
|---|---|---|---|
| CA | 2864473 A1 | 5/2013 | |
| CA | 2823592 A1 | 11/2021 | |
| CN | 101227940 A | 7/2008 | |
| CN | 103263727 A | 8/2013 | |
| CN | 104307098 A | 1/2015 | |
| EP | 0630987 A1 | 12/1994 | |
| EP | 2130326 A1 | 12/2009 | |
| EP | 2141851 A2 | 1/2010 | |
| EP | 2160127 A1 | 3/2010 | |
| EP | 2178319 A1 | 4/2010 | |
| EP | 2192897 A1 | 6/2010 | |
| EP | 2226114 A1 | 9/2010 | |
| EP | 2258496 A1 | 12/2010 | |
| EP | 2361631 A1 | 8/2011 | |
| EP | 2368401 A1 | 9/2011 | |
| EP | 2387467 A1 | 11/2011 | |
| EP | 2396995 A1 | 12/2011 | |
| EP | 2397788 A1 | 12/2011 | |
| EP | 2445990 A2 | 5/2012 | |
| EP | 2471518 A2 | 7/2012 | |
| EP | 2475283 A1 | 7/2012 | |
| EP | 2486897 A2 | 8/2012 | |
| EP | 2626051 A1 | 8/2013 | |
| EP | 2628502 A1 | 8/2013 | |
| EP | 2661307 A2 | 11/2013 | |
| EP | 2688642 A2 | 1/2014 | |
| EP | 2810689 A1 | 12/2014 | |
| EP | 2810690 A1 | 12/2014 | |
| EP | 2868343 A1 | 5/2015 | |
| EP | 2966422 A1 | 1/2016 | |
| EP | 2968940 A1 | 1/2016 | |
| EP | 3184145 A1 | 6/2017 | |
| EP | 3323468 A1 | 5/2018 | |
| EP | 3328481 A1 | 6/2018 | |
| EP | 3527258 A1 | 8/2019 | |
| JP | H0326620 A | 2/1991 | |
| JP | 3184145 B2 | 7/2001 | |
| JP | 2002200178 A | 7/2002 | |
| JP | 2007526798 A | 9/2007 | |
| JP | 2008067917 A | 3/2008 | |
| JP | 2008543429 A | 12/2008 | |
| JP | 2014514043 A | 6/2014 | |
| JP | 2016506255 A | 3/2016 | |
| JP | 2017525509 A | 9/2017 | |
| JP | 2018524113 A | 8/2018 | |
| RU | 2130326 C1 | 5/1999 | |
| RU | 2141851 C1 | 11/1999 | |
| RU | 2160127 C1 | 12/2000 | |
| RU | 2001102533 | 11/2002 | |
| RU | 2661307 C1 | 7/2018 | |
| WO | WO 1997047357 A1 | 12/1997 | |
| WO | 0234331 A2 | 5/2002 | |
| WO | WO 2002092165 A1 | 11/2002 | |
| WO | WO 2003005887 A2 | 1/2003 | |
| WO | WO 2003026735 A2 | 4/2003 | |
| WO | WO 2003092795 A1 | 11/2003 | |
| WO | WO 2004087116 A2 | 10/2004 | |
| WO | WO 2005002663 A2 | 1/2005 | |
| WO | WO 2005051306 A2 | 6/2005 | |
| WO | WO 2005065768 A1 | 7/2005 | |
| WO | WO 2005087307 A2 | 9/2005 | |
| WO | WO 2006138069 A1 | 12/2006 | |
| WO | WO 2007007058 A1 | 1/2007 | |
| WO | WO 2007012114 A1 | 2/2007 | |
| WO | 2007047852 A2 | 4/2007 | |
| WO | WO 2007057508 A2 | 5/2007 | |
| WO | WO 2007081764 A2 | 7/2007 | |
| WO | WO 2007107831 A2 | 9/2007 | |
| WO | WO 2008070807 A3 | 6/2008 | |
| WO | WO 2008075294 A1 | 6/2008 | |
| WO | WO 2008092785 A1 | 8/2008 | |
| WO | WO 2008109862 A2 | 9/2008 | |
| WO | WO 2008121891 A1 | 10/2008 | |
| WO | WO 2009042217 A1 | 4/2009 | |
| WO | WO 2009111142 A2 | 9/2009 | |
| WO | WO 2010021977 A1 | 2/2010 | |
| WO | WO 2010055421 A1 | 5/2010 | |
| WO | WO 2010114998 A1 | 10/2010 | |
| WO | WO 2010124128 A1 | 10/2010 | |
| WO | WO 2011005607 A1 | 1/2011 | |
| WO | WO 2011136875 A1 | 11/2011 | |
| WO | 2012080964 A1 | 6/2012 | |
| WO | WO 2012075195 A1 | 6/2012 | |
| WO | WO 2012094346 A2 | 7/2012 | |
| WO | WO 2012100260 A2 | 7/2012 | |
| WO | WO 2012129574 A2 | 9/2012 | |
| WO | WO 2013071307 A1 | 5/2013 | |
| WO | WO 2013071309 A1 | 5/2013 | |
| WO | WO 2013152124 A1 | 10/2013 | |
| WO | WO 2013179230 A1 | 12/2013 | |
| WO | WO 2013188965 A1 | 12/2013 | |
| WO | WO 2014005075 A1 | 1/2014 | |
| WO | WO 2014031142 A1 | 2/2014 | |
| WO | WO 2014089299 A2 | 6/2014 | |
| WO | WO 2014144785 A1 | 9/2014 | |
| WO | WO 2014149895 A1 | 9/2014 | |
| WO | WO 2014205356 A2 | 12/2014 | |
| WO | WO 2014209877 A1 | 12/2014 | |
| WO | WO 2015000800 A1 | 1/2015 | |
| WO | WO 2015048563 A2 | 4/2015 | |
| WO | WO 2015063127 A1 | 5/2015 | |
| WO | WO 2015106286 A1 | 7/2015 | |
| WO | WO 2016029159 A2 | 2/2016 | |
| WO | WO 2016033369 A1 | 3/2016 | |
| WO | WO 2016033372 A1 | 3/2016 | |
| WO | WO 2016064761 A1 | 4/2016 | |
| WO | WO 2016110804 A1 | 7/2016 | |
| WO | WO 2016112398 A1 | 7/2016 | |
| WO | WO 2016172239 A1 | 10/2016 | |
| WO | WO 2017011410 A1 | 1/2017 | |
| WO | WO 2017024276 A1 | 2/2017 | |
| WO | WO 2017035512 A1 | 3/2017 | |
| WO | WO 2017044904 A1 | 3/2017 | |
| WO | 2017062508 A1 | 4/2017 | |
| WO | WO 2017058913 A1 | 4/2017 | |
| WO | WO 2017146659 A1 | 8/2017 | |
| WO | WO 2018039296 A2 | 3/2018 | |
| WO | WO 2018106843 A1 | 6/2018 | |
| WO | WO 2018160531 A1 | 8/2018 | |
| WO | WO 2018217791 A1 | 11/2018 | |
| WO | WO 2012050200 A1 | 4/2019 | |
| WO | WO-2019211314 A1 * | 11/2019 | ............ A61B 5/002 |
| WO | WO 2020041502 A1 | 2/2020 | |
| WO | WO 2020416331 A1 | 2/2020 | |
| WO | WO 2020236946 A1 | 11/2020 | |

OTHER PUBLICATIONS

Merrill, D. et al., "Electrical stimulation of excitable tissue: design of efficacious and safe protocols," Journal of Neuroscience Methods, vol. 141, No. 2, Feb. 15, 2005, 28 pages.
Courtine, G. et al., "Transformation of nonfunctional spinal circuits into functional states after the loss of brain input," Nature Neuroscience, vol. 12, No. 10, Oct. 2009, Available Online Sep. 20, 2009, 20 pages.
Harkema, S. et al., "Effect of Epidural stimulation of the lumbosacral spinal cord on voluntary movement, standing, and assisted stepping after motor complete paraplegia: a case study," Lancet, vol. 377, No. 9781, Jun. 4, 2011, Available Online May 19, 2011, 17 pages.
Van Den Brand, R. et al., "Restoring Voluntary Control of Locomotion after Paralyzing Spinal Cord Injury," Science, vol. 336, No. 6085, Jun. 1, 2012, 5 pages.
Capogrosso, M. et al., "A Computational Model for Epidural Electrical Stimulation of Spinal Sensorimotor Circuits," The Journal of Neuroscience, vol. 33, No. 49, Dec. 4, 2013, 15 pages.
Wenger, N. et al., "Closed-loop neuromodulation of spinal sensorimotor circuits controls refined locomotion after complete spinal

(56) References Cited

OTHER PUBLICATIONS cord injury," Science Translational Medicine, vol. 6, No. 255, Sep. 24, 2014, 12 pages.

Levine, A. et al., "Identification of cellular node for motor control pathways," Nature Neuroscience, vol. 17, No. 4, Apr. 2014, Available Online Mar. 9, 2014, 22 pages.

Angeli, C. et al., "Altering spinal cord excitability enables voluntary movements after chronic complete paralysis in humans," Brain: A Journal of Neurology, vol. 137, No. 5, May 2014, Available Online Apr. 8, 2014, 16 pages.

Danner, S. et al., "Human spinal locomotor control is based on flexibly organized burst generators," Brain: A Journal of Neurology, vol. 138, No. 3, Mar. 2015, Available Online Jan. 12, 2015, 12 pages.

Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Available Online Feb. 4, 2016, 16 pages.

Capogrosso, M. et al., "A Brain-Spinal Interface Alleviating Gait Deficits after Spinal Cord Injury in Primates," Nature, vol. 539, No. 7628, Nov. 10, 2016, 39 pages.

Abernethy, J. et al., "Competing in the Dark: An Efficient Algorithm for Bandit Linear Optimization", Conference on Learning Theory, (2008), 13 pages.

Ada, L. et al., "Mechanically assisted walking with body weight support results in more independent walking than assisted overground walking in non-ambulatory patients early after stroke: a systematic review," Journal of Physiotherapy, vol. 56, No. 3, (Sep. 2010), 9 pages.

Alto, L. et al., "Chemotropic Guidance Facilitates Axonal Regeneration and Synapse Formation after Spinal Cord Injury," Nature Neuroscience, vol. 12, No. 9, Published Online Aug. 2, 2009, (Sep. 2009), 22 pages.

Anderson, K., "Targeting Recovery: Priorities of the Spinal Cord-Injured Population," Journal of Neurotrauma, vol. 21, No. 10, (Oct. 2004), 13 pages.

Auer, P. et al., "Finite-time Analysis of the Multiarmed Bandit Problem", Machine Learning, vol. 47, No. 2, (2002), pp. 235-256.

Auer, P. "Using Confidence Bounds for Exploitation-Exploration Trade-offs", Journal of Machine Learning Research, vol. 3, (2002), pp. 397-422.

Azimi, J. et al., "Batch Bayesian Optimization via Simulation Matching", In Advances in Neural Information Processing Systems (NIPS), (2010), 9 pages.

Azimi, J. et al., "Hybrid Batch Bayesian Optimization", In Proceedings of the 29th International Conference on Machine Learning, (2012), 12 pages.

Azimi, J. et al., "Batch Active Learning via Coordinated Matching", In Proceedings of the 29th International Conference on Machine Learning, (2012), 8 pages.

Barbeau, H. et al., "Recovery of locomotion after chronic spinalization in the adult cat", Brain Research, vol. 412, No. 1, (May 26, 1987), 12 pages.

Bareyre, F. et al., "The injured spinal cord spontaneously forms a new intraspinal circuit in adult rats," Nature Neuroscience, vol. 7, No. 3, Published Online Feb. 15, 2004, (Mar. 2004), 9 pages.

Basso, D. et al., "MASCIS Evaluation of Open Field Locomotor Scores: Effects of Experience and Teamwork on Reliability," Journal of Neurotrauma, vol. 13, No. 7, (Jul. 1996), 17 pages.

Brochu, et al., "A Tutorial on Bayesian Optimization of Expensive Cost Functions, with Application to Active User Modeling and Hierarchical Reinforcement Learning", In TR-2009-23, UBC, (2009), 49 pages.

Brosamle, C. et al., "Cells of Origin, Course, and Termination Patterns of the Ventral, Uncrossed Component of the Mature Rat Corticospinal Tract," The Journal of Comparative Neurology, vol. 386, No. 2, (Sep. 22, 1997), 11 pages.

Bubeck, S. et al., "Online Optimization in X-Armed Bandits", Advances in Neural Information Processing Systems (NIPS), (2008), 8 pages.

Bubeck, S. et al., "Pure Exploration in Finitely-Armed and Continuous-Armed Bandits problems" In ALT, (2009), 35 pages.

Burke, R., "Group Ia Synaptic Input to Fast and Slow Twitch Motor Units of Cat Triceps Surae", The Journal of Physiology, vol. 196, vol. 3, (Jun. 1, 1968), 26 pages.

Cai, L. et al., "Implications of Assist-As-Needed Robotic Step Training after a Complete Spinal Cord Injury on Intrinsic Strategies of Motor Learning", The Journal of Neuroscience, vol. 26, No. 41, (Oct. 11, 2006), 5 pages.

Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, (Mar. 15, 2004), 11 pages.

Colgate, E. et al., "An Analysis of Contact Instability in Terms of Passive Physical Equivalents," Proceedings of the 1989 IEEE International Conference on Robotics and Automation, Scottsdale, Arizona, (May 14, 1989), 6 pages.

Courtine, G. et al., "Can experiments in nonhuman primates expedite the translation of treatments for spinal cord injury in humans?", Nature Medicine, vol. 13, No. 5, (May 2007), 13 pages.

Courtine, G. et al., "Recovery of supraspinal control of stepping via indirect propriospinal relay connections after spinal cord injury," Nature Medicine, vol. 14, No. 1, (Jan. 6, 2008), 6 pages.

Cowley, K. et al., "Propriospinal neurons are sufficient for bulbospinal transmission of the locomotor command signal in the neonatal rat spinal cord," The Journal of Physiology, vol. 586, No. 6, Published Online Jan. 31, 2008, (Mar. 15, 2008), 13 pages.

Dani, V. et al., "Stochastic Linear Optimization Under Bandit Feedback", In Proceedings of the 21st Annual Conference on Learning Theory (COLT), (2008), 15 pages.

Danner, S. M. et al., "Body Position Influences Which neural structures are recruited by lumbar transcutaneous spinal cord stimulation", PLoS One, vol. 11, No. 1, (2016), 13 pages.

Dimitrijevic, M. M. et al., "Evidence for a Spinal Central Pattern Generator in Humans", Annals New York Academy Sciences, vol. 860, (1998), pp. 360-376.

Dimitrijevic, M. M. et al., "Clinical Elements for the Neuromuscular Stimulation and Functional Electrical Stimulation protocols in the Practice of Neurorehabilitation", Artificial Organs, vol. 26, No. 3, (2002), pp. 256-259.

Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004).

Drew, T. et al., "Cortical mechanisms involved in visuomotor coordination during precision walking," Brain Research Reviews, vol. 57, No. 1, Published Online Aug. 22, 2007, (Jan. 2007), 13 pages.

Duschau-Wicke, A. et al., "Patient-cooperative control increases active participation of individuals with SCI during robot-aided gait training," Journal of NeuroEngineering and Rehabilitation, vol. 7, No. 43, (Sep. 10, 2010), 13 pages.

Edgerton, V. et al., "Training Locomotor Networks," Brain Research Reviews, vol. 57, Published Online Sep. 16, 2007, (Jan. 2008), 25 pages.

Fleshman, J. et al., "Electronic Architecture of Type-Identified a-Motoneurons in the Cat Spinal Cord," Journal of Neurophysiology, vol. 60, No. 1, (Jul. 1, 1988), 26 pages.

Frey, M. et al., "A Novel Mechatronic Body Weight Support System," IEEE Transactions on Neural Systems and Rehabilitation Engineering, vol. 14, No. 3, (Sep. 18, 2006), 11 pages.

Fuentes, R. et al., "Spinal Cord Stimulation Restores Locomotion in Animal Models of Parkinson's Disease," Science, vol. 323, No. 5921, (Mar. 20, 2009), 14 pages.

Ganley, K. J. et al., "Epidural Spinal Cord Stimulation Improves Locomoter Performance in Low ASIA C, Wheelchair-Dependent, Spinal Cord-Injured Individuals: Insights from Metabolic Response", Top. Spinal Cord Inj. Rehabil, vol. 11, No. 2, (2005), pp. 60-63.

Gerasimenko, Yu. P. et al., "Control of Locomotor Activity in Humans and Animals in the Absence of Supraspinal Influences", Neuroscience and Behavioral Physiology, vol. 32, No. 4, (2002), pp. 417-423.

(56) References Cited

OTHER PUBLICATIONS

Gerasimenko, Yu. P. et al., "Noninvasive Reactivation of Motor Descending Control after Paralysis", Journal of Neurotrauma, vol. 32, (2015), 13 pages.
Gilja, V. et al., "A high-performance neural prosthesis enabled by control algorithm design," Nature Neuroscience, vol. 15, No. 12, Published Online Nov. 18, 2012, (Dec. 2012), 56 pages.
Gittins, J. C., "Bandit Processes and Dynamic Allocation Indices", Journal of the Royal Statistical Society B, vol. 41, No. 2, (1979), pp. 148-177.
Guyatt, G. H. et al., "The 6-minute walk: a new measure of exercise capacity in patients with chronic heart failure," Canadian Medical Association Journal, vol. 132, No. 8, (Apr. 15, 1985), 5 pages.
Hagglund, M. et al., "Activation of groups of excitatory neurons in the mammalian spinal cord or hindbrain evokes locomotion," Nature Neuroscience, vol. 13, No. 2, Published Online Jan. 17, 2010, (Feb. 2010), 8 pages.
Harrison, P. et al., "Individual Excitatory Post-Synaptic Potentials Due to Muscle Spindle Ia Afferents in Cat Triceps Surae Motoneurones," The Journal of Physiology, vol. 312, No. 1, (Mar. 1981), pp. 455-470.
Harkema, S. et al., "Human Lumbosacral Spinal Cord Interprets Loading During Stepping," Journal of Neurophysiology, vol. 77, No. 2, (Feb. 1, 1997), 15 pages.
Hashtrudi-Zaad, K. et al., "On the Use of Local Force Feedback for Transparent Teleoperation," Proceedings of the 1999 IEEE International Conference on Robotics and Automation, (May 10, 1999), 7 pages.
Hennig, P. et al., "Entropy search for information-efficient global optimization" Journal of Machine Learning Research (JMLR), vol. 13, (Jun. 2012), pp. 1809-1837.
Herman, R. et al., "Spinal cord stimulation facilitates functional walking in a chronic, incomplete spinal cord injured," Spinal Cord, vol. 40, No. 2, (2002), 4 pages.
Hidler, J. et al., "ZeroG: Overground gait and balance training system," Journal of Rehabilitation Research & Development, vol. 48, No. 4, Available as Early as Jan. 1, 2011, (2011), 12 pages.
Hines, M. L. et al., "The Neuron Simulation Environment," Neural Computation, vol. 9, No. 6, (Aug. 15, 1997), 26 pages.
Hofstoetter, U. S. et al., "Modification of Reflex Responses to Lumbar Posterior Root Stimulation by Motor Tasks in Healthy Subjects", Artificial Organs, vol. 32, No. 8, (2008), pp. 644-648.
Hofstoetter, U. S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), 149 pages.
Hofstoetter, U. S. et al., "Effects of transcutaneous spinal cord stimulation on voluntary locomotor activity in an incomplete spinal cord injured individual", Biomed Tech, vol. 58 (Suppl. 1), (2013), 3 pages.
Hofstoetter, U. S. et al., "Modification of spasticity by transcutaneous spinal cord stimulation in individuals with incomplete spinal cord injury", The Journal of Spinal Cord Medicine, vol. 37, No. 2, (2014), pp. 202-211.
Ivanenko, Y. P. et al., "Temporal Components of the Motor Patterns Expressed by the Human Spinal Cord Reflect Foot Kinematics," Journal of Neurophysiology, vol. 90, No. 5, Nov. 2003, Published Online Jul. 9, 2003, (2003), 11 pages.
Jarosiewicz, B. et al., "Supplementary Materials for Virtual typing by people with tetraplegia using a self-calibrating intracortical brain-computer interface," Science Translational Medicine, vol. 7, No. 313, (Nov. 11, 2015), 26 pages.
Jarosiewicz, B. et al., "Virtual typing by people with tetraplegia using a self-calibrating intracortical brain-computer interface," Science Translational Medicine, vol. 7, No. 313, (Nov. 11, 2015), 11 pages.
Jilge, B. et al., "Initiating extension of the lower limbs in subjects with complete spinal cord injury by epidural lumbar cord stimulation", Exp Brain Res., vol. 154, (2004), pp. 308-326.
Johnson, W. L. et al., "Application of a Rat Hindlimb Model: A Prediction of Force Spaces Reachable Through Stimulation of Nerve Fascicles," IEEE Transactions on Bio-Medical Engineering, vol. 58, No. 12, Available Online Jan. 17, 2011, (Dec. 2011), 22 pages.
Jones, K. E. et al., "Computer Simulation of the Responses of Human Motoneurons to Composite 1A EPSPS: Effects of Background Firing Rate," The Journal of Physiology, vol. 77, No. 1, (1997), 16 pages.
Jones, D. R. et al., "Efficient Global Optimization of Expensive Black-Box Functions", Journal of Global Optimization, vol. 13, (1998), pp. 455-492.
Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Published Online Jul. 17, 2000, (Aug. 1, 2000), 2 pages.
Kleinberg, R. et al., "Multi-armed bandits in metric spaces", In STOC, Computer and Automation Research Institute of the Hungarian Academy of Sciences, Budapest, Hungary, (2008), pp. 681-690.
Kocsis, L. et al. "Bandit Based Monte-Carlo Planning", European Conference on Machine Learning, Springer, Berlin, Heidelberg, (Sep. 2006), pp. 282-293.
Krassioukov, A. et al., "A Systematic Review of the Management of Autonomic Dysreflexia Following Spinal Cord Injury," Archives of Physical Medicine and Rehabilitation, vol. 90, No. 4, (Apr. 2009), 27 pages.
Krassioukov, A. et al., "A Systematic Review of the Management of Orthostatic Hypotension Following Spinal Cord Injury," Archives of Physical Medicine and Rehabilitation, vol. 90, No. 5, (May 2009), 22 pages.
Krause, A. et al., "Near-optimal Nonmyopic Value of Information in Graphical Models", In UAI, (2005), 8 pages.
Krause, A. et al. "Near-Optimal Sensor Placements in Gaussian Processes: Theory, Efficient Algorithms and Empirical Studies", Journal of Machine Learning Research (JMLR), vol. 9, (Feb. 2008), pp. 235-284.
Krause, A. et al. "Contextual Gaussian Process Bandit Optimization", In Advances in Neural Information Processing Systems (NIPS), (2011), 9 pages.
Kwakkel, G. et al., "Effects of Robot-assisted therapy on upper limb recovery after stroke: A Systematic Review," Neurorehabilitation and Neural Repair, vol. 22, No. 2, Published Online Sep. 17, 2007, (Mar. 2008), 17 pages.
Ladenbauer, J. et al., "Stimulation of the human lumbar spinal cord with implanted and surface electrodes: a computer simulation study", IEEE Transactions on Neural Systems and Rehabilitation Engineering, vol. 18, No. 6, (2010), pp. 637-645.
Lavrov, I. et al., "Epidural Stimulation Induced Modulation of Spinal Locomotor Networks in Adult Spinal Rats," Journal of Neuroscience, vol. 28, No. 23, (Jun. 4, 2008), 8 pages.
Liu, J. et al., "Stimulation of the Parapyramidal Region of the Neonatal Rat Brain Stem Produces Locomotor-Like Activity Involving Spinal 5-HT$_7$ and 5-HT$_{2A}$ Receptors", Journal of Neurophysiology, vol. 94, No. 2, Published Online May 4, 2005, (Aug. 1, 2005), 13 pages.
Lizotte, D. et al., "Automatic gait optimization with Gaussian process regression", In IJCAI, (2007), pp. 944-949.
Lovely, R. et al., "Effects of Training on the Recovery of Full-Weight-Bearing Stepping in the Adult Spinal Cat," Experimental Neurology, vol. 92, No. 2, (May 1986), 15 pages.
Lozano, A. et al., "Probing and Regulating Dysfunctional Circuits Using Deep Brain Stimulation," Neuron, vol. 77, No. 3, (Feb. 6, 2013), 19 pages.
McIntyre, C. C. et al., "Modeling the Excitability of Mammalian Nerve Fibers: Influence of Afterpotentials on the Recovery Cycle," Journal of Neurophysiology, vol. 87, No. 2, (Feb. 2002), 12 pages.
Minassian, K. et al., "Stepping-like movements in humans with complete spinal cord injury induced by epidural stimulation of the lumbar cord: electromyographic study of compound muscle action potentials", Spinal Cord, vol. 42, (2004), pp. 401-416.

(56) References Cited

OTHER PUBLICATIONS

Minassian, K. et al., "Peripheral and Central Afferent Input to the Lumbar Cord", Biocybernetics and Biomedical Engineering, vol. 25, No. 3, (2005), pp. 11-29.

Minassian, K. et al., "Human lumbar cord circuitries can be activated by extrinsic tonic input to generate locomotor-like activity", Human Movement Science, vol. 26, No. 2, (2007), pp. 275-295.

Minassian, K. et al., "Posterior root-muscle reflex", Second Congress International Society of Intraoperative Neurophysiology (ISIN), Dubrovnik, Croatia, (2009), pp. 77-80.

Minassian, K. et al., "Transcutaneous stimulation of the human lumbar spinal cord: Facilitating locomotor output in spinal cord injury", Society for Neuroscience, Conference Proceedings, Neuroscience 2010, San Diego, CA, Abstract Viewer/ Itinerary Planner No. 286. 19, Abstract & Poster attached (2010), 1 page.

Minassian, K. et al., "Neuromodulation of lower limb motor control in restorative neurology", Clinical Neurology and Neurosurgery, vol. 114, (2012), pp. 489-497.

Minassian et al., "Mechanisms of rhythm generation of the human lumbar spinal cord in repose to tonic stimulation without and with step-related sensory feedback", Biomed Tech, vol. 58, (Suppl. 1), (2013), 3 pages.

Minev, I. R. et al., "Electronic dura mater for long-term multimodal neural interfaces," Science Magazine, vol. 347, No. 6218, (Jan. 9, 2015), 64 pages.

Minoux, M., Accelerated greedy algorithms for maximizing submodular set functions. Optimization Techniques, LNCS, (1978), pp. 234-243.

Murg, M. et al., "Epidural electric stimulation of posterior structures of the human lumbar spinal cord: 1. Muscle twitches—a functional method to define the site of stimulation", Spinal Cord, vol. 38, (2000), pp. 394-402.

Musienko, P. et al. "Multi-system neurorehabilitative strategies to restore motor functions following severe spinal cord injury," Experimental Neurology, vol. 235, No. 1, Published Online Sep. 7, 2011, (May 2012), 10 pages.

Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Published Online Jul. 24, 2009, (Nov. 2009), 5 pages.

Musienko, P. et al., "Controlling specific locomotor behaviors through multidimensional monoaminergic modulation of spinal circuitries," The Journal of Neuroscience, vol. 31, No. 25, (Jun. 22, 2011), 32 pages.

Musselman, K. et al., "Spinal Cord Injury Functional Ambulation Profile: A New Measure of Walking Ability," Neurorehabilitation and Neural Repair, vol. 25, No. 3, Published Online Feb. 25, 2011, (Mar. 2011), 9 pages.

Nan, D. et al., "Life-threatening outcomes associated with autonomic dysreflexia: A clinical review," Journal of Spinal Cord Medicine, vol. 37, No. 1, (Jan. 2014), 9 pages.

Nandra, M. S. et al., "A parylene-based microelectrode array implant for spinal cord stimulation in rats", Conference Proceedings IEEE Eng. Med. Biol. Soc., (2011), pp. 1007-1010.

Nandra, M. S. et al., "A wireless microelectrode implant for spinal cord stimulation and recording in rats", Presentation Abstract, 2013.

Nessler, J. et al., "A Robotic Device for Studying Rodent Locomotion After Spinal Cord Injury," IEEE Transactions on Neural Systems and Rehabilitation Engineering, vol. 13, No. 4, (Dec. 12, 2005), 10 pages.

Pearson, K. G., "Generating the walking gait: role of sensory feedback," Progress in Brain Research, vol. 143, Chapter 12, Published Online Nov. 28, 2003, (2004), 7 pages.

Phillips, A. et al., "Perturbed and spontaneous regional cerebral blood flow responses to changes in blood pressure secondary high-level spinal cord injury: the effect of midodrine," Journal of Applied Physiology, vol. 116, No. 6, Available Online Jan. 16, 2014, (Mar. 15, 2014), 20 pages.

Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, (May 2014), 8 pages.

Phillips, A. A. et al., "Contemporary Cardiovascular Concerns after Spinal Cord Injury: Mechanisms, Maladaptations, and Management," Journal of Neurotrama, vol. 32, No. 24, (Dec. 15, 2015), 17 pages.

Pratt, G. et al., "Stiffness Isn't Everything," Proceedings of the Fourth International Symposium on Experimental Robotics, (Jun. 30, 1995), 6 pages.

Pratt, J. et al., "Series elastic actuators for high fidelity force control," Industrial Robot: An International Journal, vol. 29, No. 3, Available as Early as Jan. 1, 2002, (1995), 13 pages.

Prochazka, A. et al., "Ensemble firing of muscle afferents recorded during normal locomotion in cats," The Journal of Physiology, vol. 507, No. 1, (Feb. 15, 1998), 12 pages.

Prochazka, A. et al., "Models of ensemble filing of muscle spindle afferents recorded during normal locomotion in cats," The Journal of Physiology, vol. 507, No. 1, (Feb. 15, 1998), 15 pages.

Pudo, D. et al., "Estimating Intensity Fluctuations in High Repetition Rate Pulse Trains Generated Using the Temporal Talbot Effect", IEEE Photonics Technology Letters, vol. 18, No. 5, (Mar. 1, 2006), 3 pages.

Rasmussen, C. E. et al., "Gaussian Processes for Machine Learning", The MIT Press, Cambridge, Massachusetts, (2006), 266 pages.

Rasmussen, C. E. et al., "Gaussian Processes for Machine Learning (GPML) Toolbox", The Journal of Machine Learning Research, vol. 11, (2010), pp. 3011-3015.

Rasmussen, C. E. "Gaussian Processes in Machine Learning", L.N.A.I., vol. 3176, (2003) pp. 63-71.

Rattay, F. et al., "Epidural electrical stimulation of posterior structures of the human lumbosacral cord: 2. Quantitative analysis by computer modeling", Spinal Cord, vol. 38, (2000), pp. 473-489.

Reinkensmeyer, D. et al., "Tools for understanding and optimizing robotic gait training," Journal of Rehabilitation Research & Development, vol. 43, No. 5, (Aug. 2006), 14 pages.

Rejc, E. et al., "Effects of Lumbosacral Spinal Cord Epidural Stimulation for Standing after Chronic Complete Paralysis in Humans," PLoS One, vol. 10, No. 7, (Jul. 24, 2015), 20 pages.

Robbins, H., "Some Aspects of the Sequential Design of Experiments", Bull. Amer. Math. Soc., vol. 58, (1952), pp. 527-535.

Rodger, D. C. et al., "High Density Flexible Parylene-Based Multielectrode Arrays for Retinal and Spinal Cord Stimulation", Proc. of the 14th International Conference on Solid-State Sensors, Actuators and Microsystems, (2007), pp. 1385-1888.

Rosenzweig, E. et al., "Extensive Spontaneous Plasticity of Corticospinal Projections After Primate Spinal Cord Injury", Nature Neuroscience, vol. 13, No. 12, Published Online Nov. 14, 2010, (Dec. 2010), 19 pages.

Ryzhov, I. O. et al., "The knowledge gradient algorithm for a general class of online learning problems", Operations Research, vol. 60, No. 1, (2012), pp. 180-195.

Sayenko, D. et al., "Neuromodulation of evoked muscle potentials induced by epidural spinal-cord stimulation in paralyzed individuals," Journal of Neurophysiology, vol. 111, No. 5, Published Online Dec. 11, 2013, (2014), 12 pages.

Shamir, R. R. et al., "Machine Learning Approach to Optimizing Combined Stimulation and Medication Therapies for Parkinson's Disease," Brain Stimulation, vol. 8, No. 6, Published Online Jun. 15, 2015, (Nov. 2015), 22 pages.

Srinivas, N. et al., "Gaussian process optimization in the bandit setting: No regret and experimental design", In Proceedings of the 27th International Conference on Machine Learning, (2010), 17 pages.

Steward, O. et al., "False Resurrections: Distinguishing Regenerated from Spared Axons in the Injured Central Nervous System", The Journal of Comparative Neurology, vol. 459, No. 1, (Apr. 21, 2003), 8 pages.

Stienen, A. H. A. et al., "Analysis of reflex modulation with a biologically realistic neural network," Journal of Computer Neuroscience, vol. 23, No. 3, Available Online May 15, 2007, (Dec. 2007), 16 pages.

(56) References Cited

OTHER PUBLICATIONS

Sun, F. et al., "Sustained axon regeneration induced by co-deletion of PTEN and SOCS3", Nature, vol. 480, No. 7377, Published Online Nov. 6, 2011, (Dec. 15, 2011), 12 pages.
Takeoka, A. et al., "Muscle Spindle Feedback Directs Locomotor Recovery and Circuit Reorganization after Spinal Cord Injury", Cell, vol. 159, No. 7, (Dec. 18, 2014), 27 pages.
Tenne, Y. et al., "Computational Intelligence in Expensive Optimization Problems", vol. 2 of Adaptation, Learning, and Optimization, Springer, Berlin Heidelberg, (2010), pp. 131-162.
Timozyk, W. et al., "Hindlimb loading determines stepping quantity and quality following spinal cord transection," Brain Research, vol. 1050, No. 1-2, Published Online Jun. 24, 2005, (Jul. 19, 2005), 10 pages.
Vallery, H. et al., "Compliant Actuation of Rehabilitation Robots," IEEE Robotics & Automation Magazine, vol. 15, No. 3, (Sep. 12, 2008), 10 pages.
Wan, D. et al., "Life-threatening outcomes associated with autonomic dysreflexia: A clinical review," Journal of Spinal Cord Medicine, vol. 37, No. 1, Jan. 2014, 9 pages.
Ward, A. R., "Electrical Stimulation Using Kilohertz-Frequency Alternating Current", Physical Therapy, vol. 89, Published online Dec. 18, 2008, (2009), pp. 181-190.
Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.
Wenger, N. et al., "Spatiotemporal neuromodulation therapies engaging muscle synergies improve motor control after spinal cord injury," Natural Medicine, vol. 22, No. 2, Available Online Jan. 18, 2016, (Feb. 2016), 33 pages.
Wernig, A. et al., "Laufband locomotion with body weight support improved walking in persons with severe spinal cord injuries", Paraplegia, vol. 30, No. 4, (Apr. 1992), 10 pages.
Wernig, A., "Ineffectiveness—of Automated Locomotor Training," Archives of Physical Medicine and Rehabilitation, vol. 86, No. 12, (Dec. 2005), 2 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, (Jun. 2010), 7 pages.
Widmer, C. et al., Inferring latent task structure for multitask learning by multiple kernel learning, BMC Bioinformatics, vol. 11, (Suppl 8:S5), (2010), 8 pages.
Winter, D. A. et al., "An integrated EMG/biomechanical model of upper body balance and posture during human gait," Progress in Brain Research, vol. 97, Ch. 32, Available as Early as Jan. 1, 1993, (1993), 9 pages.
Wirz, M. et al., "Effectiveness of automated locomotor training in patients with acute incomplete spinal cord injury: A randomized controlled multicenter trial," BMC Neurology, vol. 11, No. 60, (May 27, 2011), 9 pages.
Yakovenko, S. et al., "Spatiotemporal Activation of Lumbosacral Motoneurons in the Locomotor Step Cycle," Journal of Neurophysiology, vol. 87, No. 3, (Mar. 2002), 12 pages.
Zhang, T. C. et al., "Mechanisms and models of spinal cord stimulation for the treatment of neuropathic pain," Brain Research, vol. 1569, Published Online May 4, 2014, (Jun. 20, 2014), 13 pages.
Zorner, B. et al., "Profiling locomotor recovery: comprehensive quantification of impairments after CNS damage in rodents," Nature Methods, vol. 7, No. 9, Published Online Aug. 15, 2010, (Sep. 2010), 11 pages.

* cited by examiner

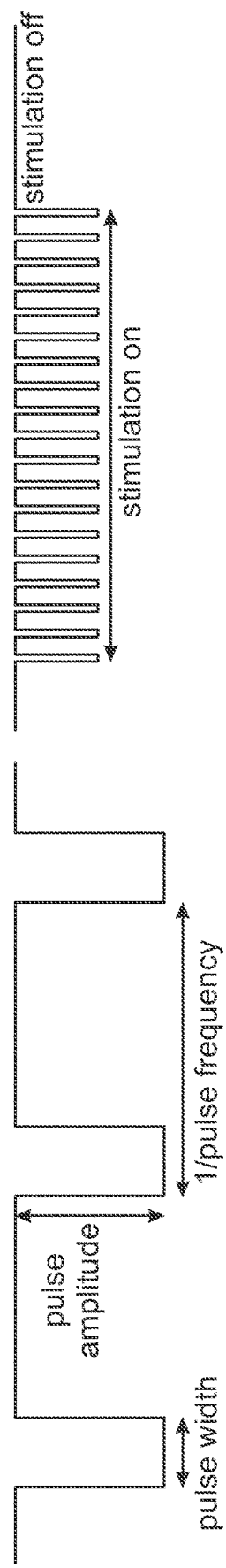

| Fiber type | Diameter (μm) | Function |
|---|---|---|
| Ia (A-α) | 12-20 | Proprioception from muscle spindles |
| Ib (A-α) | 12-20 | Proprioception from Golgi tendon organs |
| II (A-β) | 5-12 | Fine touch, (2-point discrimination & vibration) |
| III (A-δ) | 2-5 | Light touch, fast pain & temperature |
| IV (C) | 0.5-1 | Slow pain & temperature |

Fig. 3

| # | FMB | Agonist | Antagonist |
|---|---|---|---|
| 1 | Right Ankle Extension | Right medial gastrocnemius, soleus | Right tibialis anterior |
| 2 | Right Ankle Flexion | Right tibialis anterior | Right medial gastrocnemius, soleus |
| 3 | Right Knee Extension | Right rectus femoris, vastus lateralis | Right iliopsoas, semitendinosus |
| 4 | Right Hip Extension | Right gluteus maximus, semitendinosus | Right iliopsoas, rectus femoris |
| 5 | Right Hip Flexion | Right iliopsoas, rectus femoris | Right gluteus maximus, semitendinosus |
| 6 | Right Trunk Stability | Right paraspinal muscles | |
| 7 | Left Ankle Extension | Left medial gastrocnemius, soleus | Left tibialis anterior |
| 8 | Left Ankle Flexion | Left tibialis anterior | Left medial gastrocnemius, soleus |
| 9 | Left Knee Extension | Left rectus femoris, vastus lateralis | Left iliopsoas, semitendinosus |
| 10 | Left Hip Extension | Left gluteus maximus, semitendinosus | Left iliopsoas, rectus femoris |
| 11 | Left Hip Flexion | Left iliopsoas, rectus femoris | Left gluteus maximus, semitendinosus |
| 12 | Left Trunk Stability | Left paraspinal muscles | |

Fig. 5

FMB/CMB used in Task 1

| Right | Left |
|---|---|
| RIGHT ANKLE EXTENSION | LEFT ANKLE EXTENSION |
| RIGHT ANKLE FLEXION | LEFT ANKLE FLEXION |
| RIGHT KNEE EXTENSION | LEFT KNEE EXTENSION |
| RIGHT HIP EXTENSION | LEFT HIP EXTENSION |
| RIGHT HIP FLEXION | LEFT HIP FLEXION |
| RIGHT TRUNK STABILITY | LEFT TRUNK STABILITY |
| CUSTOM FUNCTIONAL BLOCK 1 | CUSTOM FUNCTIONAL BLOCK N |

FMB/CMB used in Task 2

| Right | Left |
|---|---|
| RIGHT ANKLE EXTENSION | LEFT ANKLE EXTENSION |
| RIGHT ANKLE FLEXION | LEFT ANKLE FLEXION |
| RIGHT KNEE EXTENSION | LEFT KNEE EXTENSION |
| RIGHT HIP EXTENSION | LEFT HIP EXTENSION |
| RIGHT HIP FLEXION | LEFT HIP FLEXION |
| RIGHT TRUNK STABILITY | LEFT TRUNK STABILITY |
| CUSTOM FUNCTIONAL BLOCK 1 | CUSTOM FUNCTIONAL BLOCK N |

Fig. 6

CONTROL SYSTEM FOR MOVEMENT RECONSTRUCTION AND/OR RESTORATION FOR A PATIENT

CROSS-REFERENCE TO RELATED APPLICATIONS

The present application claims priority to European Patent Application No. 18205821.4 and filed on Nov. 13, 2018. The entire contents of the above-listed application is hereby incorporated by reference for all purposes.

TECHNICAL FIELD

The present invention relates to a system for controlling a movement reconstruction and/or restoration system for a patient, e.g. in the field of improving recovery after neurological disorders like spinal cord injury (SCI), for example after trauma.

BACKGROUND AND SUMMARY

Decades of research in physiology have demonstrated that the mammalian spinal cord embeds sensorimotor circuits that produce movement primitives (cf. Bizzi E., et al., *Modular organization of motor behavior in the frog's spinal cord*. Trends in neurosciences 18, 442-446 (1995); Levine A. J. et al., *Identification of a cellular node for motor control pathways*. Nature neuroscience 17, 586-593 (2014)). These circuits process sensory information arising from the moving limbs and descending inputs originating from various brain regions in order to produce adaptive motor behaviors.

A spinal cord injury (SCI) interrupts the communication between the spinal cord and supraspinal centres, depriving these sensorimotor circuits from the excitatory and modulatory drives necessary to produce movement.

A series of studies in animal models and humans showed that electrical neuromodulation of the lumbar spinal cord using epidural electrical stimulation (EES) is capable of (re-)activating these circuits. For example, EES has restored coordinated locomotion in animal models of SCI, and isolated leg movements in individuals with motor paralysis (cf. van den Brand R., et al., *Restoring Voluntary Control of Locomotion after Paralyzing Spinal Cord Injury*. Science 336, 1182-1185 (2012); Angeli C A. et al., *Altering spinal cord excitability enables voluntary movements after chronic complete paralysis in humans*. Brain: a journal of neurology 137, 1394-1409 (2014); Harkema S. et al., *Effect of epidural stimulation of the lumbosacral spinal cord on voluntary movement, standing, and assisted stepping after motor complete paraplegia: a case study*. The Lancet 377, 1938-1947 (2011); Danner S M et al., *Human spinal locomotor control is based on flexibly organized burst generators*. Brain: a journal of neurology 138, 577-588 (2015); Courtine G. et al., *Transformation of nonfunctional spinal circuits into functional states after the loss of brain input*. Nature neuroscience 12, 1333-1342, (2009); Capogrosso M et al., *A brainspine interface alleviating gait deficits after spinal cord injury in primates*. Nature 539, 284-288 (2016)).

EP 2 868 343 A1 discloses a system to deliver adaptive electrical spinal cord stimulation to facilitate and restore locomotion after neuromotor impairment. Inter alia, a closed-loop system for real-time control of epidural electrical stimulation is disclosed, the system comprising means for applying to a subject neuromodulation with adjustable stimulation parameters, said means being operatively connected with a real-time monitoring component comprising sensors continuously acquiring feedback signals from said subject. The feedback signals provide features of motion of a subject, wherein the real-time monitoring component is operatively connected with a signal processing device receiving feedback signals and operating real-time automatic control algorithms. This known system improves consistency of walking in a subject with a neuromotor impairment. A Real Time Automatic Control Algorithm is used, comprising a feedforward component employing a single input-single output model (SISO), or a multiple input-single output (MISO) model. Reference is also made to Wenger N. et al., *Closed-loop neuromodulation of spinal sensorimotor circuits controls refined locomotion after complete spinal cord injury*, Science Translational Medicine, 6, 255 (2014).

WO 2002/034331 A2 discloses a non-closed loop implantable medical device system that includes an implantable medical device, along with a transceiver device that exchanges data with the patient, between the patient and the implantable medical device, and between a remote location and the implantable medical device. A communication device coupled to the transceiver device exchanges data with the transceiver device, the implantable medical device through the receiver device, and between the transceiver device and the remote location to enable bi-directional data transfer between the patient, the implantable medical device, the transceiver device, and the remote location. A converter unit converts transmission of the data from a first telemetry format to a second telemetry format, and a user interface enables information to be exchanged between the transceiver device and the patient, between the implantable medical device and the patient through the transceiver device, and between the patient and the remote location through the transceiver device.

EP 3 184 145 A1 discloses systems for selective spatiotemporal electrical neurostimulation of the spinal cord. A signal processing device receiving signals from a subject and operating signal-processing algorithms to elaborate stimulation parameter settings is operatively connected with an Implantable Pulse Generator (IPG) receiving stimulation parameter settings from said signal processing device and able to simultaneously deliver independent current or voltage pulses to one or more multiple electrode arrays. The electrode arrays are operatively connected with one or more multi-electrode arrays suitable to cover at least a portion of the spinal cord of said subject for applying a selective spatiotemporal stimulation of the spinal circuits and/or dorsal roots, wherein the IPG is operatively connected with one or more multi-electrode arrays to provide a multipolar stimulation. Such system allows achieving effective control of locomotor functions in a subject in need thereof by stimulating the spinal cord, in particular the dorsal roots, with spatiotemporal selectivity.

EP 2 652 676 A1 relates to a gesture control for monitoring vital body signs and reuses an accelerometer, or, more precise, sensed accelerations of a body sensor for user control of the body sensor. This is achieved by detecting predefined patterns in the acceleration signals that are unrelated to other movements of the patient. These include tapping on/with the sensor, shaking, and turning the sensor. New procedures are described that make it possible to re-use the acceleration sensing for reliable gesture detection without introducing many false positives due to non-gesture movements like respiration, heartbeat, walking, etc. Similar solutions for tapping detection of a user are known from U.S. Pat. Nos. 8,326,569 and 7,742,037.

WO 2007/047852 A2 discloses systems and methods for patient interactive neural stimulation and/or chemical substance delivery. A method in accordance with one embodiment of the invention includes affecting a target neural population of the patient by providing to the patient at least one of an electromagnetic signal and a chemical substance. The method can further include detecting at least one characteristic of the patient, which is correlated with the patient's performance of an adjunctive therapy task that is performed in association with affecting the target neural population. Further, this method can include controlling at least one parameter in accordance with which the target neural population is affected, based at least in part on the detected characteristic.

WO 2017/062508 A1 discloses a system for controlling a therapeutic device and/or environmental parameters including one or more body worn sensor devices that detect and report one or more physical, physiological, or biological parameters of a person in an environment. The sensor devices can communicate sensor data indicative of the physical, physiological, or biological parameters of a person to an external hub that processes the data and communicates with the therapeutic device to provide a therapy (e.g., neuromodulation, neurostimulation, or drug delivery) as a function of the sensor data.

According to the state of the art, voluntary control of movement still cannot be achieved by the subject. It is important to keep in mind that the patient is not a robot and can and should not be stimulated and controlled as a robot. Therefore, there is a lack to have a system which overcomes the drawbacks of the prior art. In particular, there is the need of a system stimulating the patient not as a robot. The goal of applying stimulation is not to control the patient, but to support the patient during training and daily life activities. Hence, a control system should support the patient's own natural control loop composed of the brain, nervous system, and sensory organs. This means that said control system should not e.g. adjust the stimulation parameters to force the patient's lower body motion to a given reference trajectory. Instead, the patient should be able to determine e.g. the walking cadence.

It is an object of the present invention to improve a neurostimulation system, e.g. in the field of improving recovery after neurological disorders like spinal cord injury, for example after trauma, especially in adding a control system for a movement reconstruction and/or restoration system for a patient.

This object is solved according to the present invention by a control system for a movement reconstruction and/or restoration system for a patient, with the features of claim 1. Accordingly, a system for a movement reconstruction and/or restoration system for a patient, comprising
    at least one sensor,
    at least one controller,
    at least one programmer,
    at least one stimulation system,
wherein the controller is connected with the sensor, the programmer and the stimulation system, wherein the sensor is part of or attached to a training entity in order to create and/or guide a movement model for a patient and/or
    adjust stimulation settings based on sensor input.

The invention is based on the basic idea that in the context of neuromodulation, especially neurostimulation, the electrical stimulation parameters defining the stimulation in a movement reconstruction and/or restoration system for a patient can be controlled with said system, wherein a training entity is used, which is not the patient himself or herself, but another entity. By this, a more defined or even a remote training and rehabilitation is possible. The use of a general hardware concept and sensors being part of or being attached to a training entity combined into one strategy and made available for a patient being equipped with the system allow to support limbs, e.g. lower limbs motor function of patients with complete or incomplete SCI to enable rehabilitation training and facilitate daily life activities. The training entity defines movement, including but not limited to gait phase in terms of kinematics of the body and/or parts of the body, e.g. lower body (legs and feet), upper body (trunk, head, arms, hands). Hence, to estimate the movement, body kinematics need to be determined.

To estimate the gait phase, in particular the lower body kinematics need to be determined. This can be done directly by attaching sensors to the body and/or parts of the body including but not limited to parts of the trunk and/or abdomen and/or the limbs and/or part of the limbs or indirectly by measuring muscle activation or by measuring the interaction between the body and/or parts of the body, e.g. limbs and/or part of the limbs and their surroundings (e.g. the ground reaction forces or upper body motion). Based on this, the system enables stimulating the spinal cord at the correct place and at the correct time while the patient is performing different tasks. This means that the control system does not e.g. adjust the stimulation parameters to force the patient's body and/or limb(s) motion to a given reference trajectory.

Moreover, the general feeling and well-being (e.g. pain treatment) of the patient can be enhanced.

The programmer is an application installed on a mobile device that communicates with the controller. The programmer is used by the therapist, physiotherapist, or patient to provide inputs to the controller, e.g., selecting, starting, and stopping a task or configuring stimulation parameters.

The programmer should allow adjusting the stimulation parameters of a task, while the task is running. This enables the user to tune the stimulation without having to start and stop the task, which would be very cumbersome at the start of the rehabilitation training, when all stimulation partitures are developed and tuned.

The programmer includes but is not limited to a physiotherapist programmer (PTP), and patient programmer (PP) which are applications installed on a mobile device that communicate with the controller.

Neural stimulation may be achieved by electrical stimulation, optogenetics (optical neural stimulation), chemical stimulation (implantable drug pump), ultrasound stimulation, magnetic field stimulation, mechanical stimulation, etc.

Known electrical stimulation systems use either Central Nervous System (CNS) stimulation, especially Epidural Electrical Stimulation (EES), or Peripheral Nervous System (PNS) Stimulation, especially Functional Electrical Stimulation (FES).

Epidural Electrical Stimulation (EES) is known to restore motor control in animal and human models and has more particularly been shown to restore locomotion after spinal cord injury by artificially activating the neural networks responsible for locomotion below the spinal cord lesion (Capogrosso, M, et al., *A Computational Model for Epidural Electrical Stimulation of Spinal Sensorimotor Circuits, Journal of Neuroscience,* 33 (49), 19326-19340 (2013); Courtine G., et al., *Transformation of nonfunctional spinal circuits into functional states after the loss of brain input, Nat Neurosci.* 12(10), 1333-1342 (2009); Moraud E M., et al, *Mechanisms Underlying the Neuromodulation of Spinal Circuits for Correcting Gait and Balance Deficits after Spinal Cord Injury, Neuron,* 89(4), 814-828 (2016)). EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies.

Peripheral Nervous System (PNS) Stimulation systems used to date in the clinic are known as Functional Electrical Stimulation (FES) that provides electrical stimulation to target muscles with surface electrodes, either directly through stimulation of their motorfibers (neuro-muscular stimulation), or through a limited set reflexes (practically limited to the withdrawal reflex) or by transcutaneously stimulating the peripheral nerves. The resulting muscle fatigue has rendered FES unsuitable for use in daily life. Furthermore, successes have remained limited through cumbersome setups when using surface muscle stimulation, unmet needs in terms of selectivity (when using transcutaneous nerve stimulation) and a lack of stability (impossible to reproduce exact electrode placement on a daily basis when stimulating muscles, moving electrodes due to clothes, sweating).

It is possible to provide neuromodulation and/or neurostimulation with the system to the CNS with a CNS stimulation system and/or to the PNS with a PNS stimulation system. Both CNS and PNS can be stimulated at the same time or also intermittently or on demand. These two complementary stimulation paradigms can be combined into one strategy and made available for a patient being equipped with the system. For example, neuromodulation and/or neurostimulation of the CNS may be used to enhance and/or the patient's capabilities of movement, especially in a way that the existing ways of physiological signal transfer in the patient's body is supported such that the command signals for body movement or the like still are provided by the patient's nervous system and just supported and/or enhanced or translated by the CNS stimulation system. The stimulation provided by the PNS system may be used to specifically steer and direct stimulation signals to specific peripheral nervous structures in order to trigger a specific movement and/or refine existing movements. Such a PNS stimulation may be used to refine and/or complete motion and/or the patient's capabilities of movement. It can be e.g. used to complete flexion or extension, lifting, turning or the like of inter alia but not limited to toes, fingers, arms, feet, legs or any extremities of the patient. This can be e.g. done in cases where it is realized that the neuromodulation and/or neurostimulation provided by the CNS stimulation system is not sufficient to complete a movement or intended status of the patient. Then, such a movement or intended status may be completed or supported by stimulation provided by the PNS stimulation system. The PNS stimulation can be also used to reduce side effects or compensate for imprecisions of the CNS stimulation.

EES can be phasic or tonic, selective PNS is always phasic. Phasic is defined as locked to defined events in the sensing signals (decoded intention, continuous decoding, muscle activity onset, movement onset, event during defined movement (foot off or foot strike during gait for instance).

By PNS stimulation, a stimulation of the upper limb nerves, i.e. the radial, ulnar and/or median nerves can be provided. Also, the lower limb nerves like the sciatic and/or femoral nerves can be provided in PNS stimulation. All PNS stimulation can be done by targeting one of the above-mentioned nerves with intra-neural electrodes (transversal or longitudinal) or epi-neural (cuff) electrodes.

By CNS stimulation the following nervous structures may be stimulated: for the upper limb movements the cervical spinal cord or hand/arm motor cortex may be stimulated with the CNS stimulation system. For the lower limb movements, the lumbosacral spinal cord may be stimulated. All these nerves can be targeted with epidural, subdural or intra-spinal/intra-cortical stimulation.

Both PNS and CNS stimulation systems may comprise implantable pulse generators (IPGs). IPGs can be used for providing the necessary stimulation current and signals for the CNS stimulation system and the PNS stimulation system.

The IPG produces the stimulation pulses that are delivered by a lead with multiple electrodes to the stimulation side, e.g. spinal cord. For EES, the lead is positioned in the epidural space (i.e. on the outside of the dural sac, which encases the spinal cord and the cerebrospinal fluid in which the spinal cord 'floats'), on top of the spinal cord (including, but not limited to the segments T12, L1, L2, L3, L4, L5, and S1 bilaterally).

It is also possible that two separated IPGs are provided, one for the PNS stimulation system and one for the CNS stimulation system.

It is also possible that external stimulators are used, especially for PNS stimulation. The stimulation parameters for the PNS stimulation and the EES stimulation may be frequency, amplitude, pulse-width and the like.

The system may support open-loop or closed-loop stimulation modes. Open-loop stimulation may be performed where a pre-defined fixed stimulation is executed without adapting to e.g. the motion of the patient. The stimulation settings (i.e. electrode configuration—that means stimulation delivery by which electrode to stimulate which functional muscle block at which times, frequencies, and amplitudes) are determined completely by the therapist or physiotherapist and/or field engineer and/or algorithmically. The control system may interfere with the natural feedback loop of the patient to enable smooth motion, e.g. a regular gait cycle comparable to a healthy subject. Closed-loop walking may be performed, where feedback is used to adjust the stimulation to the gait of the patient. Closed-loop cycling may be performed, where feedback is used to adjust the stimulation to the cycling phase of the patient.

The interfaces wireless sensor network WSN (wireless link between the sensors and the controller), communication COM (wireless link between a programmer and the controller), and telemetry TEL (wireless link between the stimulation system and the controller) connect the various subsystems in the control loop.

Programmers are mobile devices, the stimulation system is implanted in the body, the controller is body-worn, and the sensors are attached to the patient's body and/or one or more parts of the patient's body and/or the patient's limbs/feet or to a bicycle crank and/or to any other training apparatus for any other type of movement, including but not limited to rowing, stepping and/or swimming. Hence, these interfaces all need to be wireless.

The training entity may be a trainer and/or physiotherapist.

In particular, the shoe of the patient and/or physiotherapist may be equipped with sensors. Said sensors may be placed on top of the instep of the shoe, and/or at the back of the heel and/or below the heel of the shoe (e.g. in a pocket in the sole of the shoe or as an inlay sole) of the patient and/or physiotherapist.

Moreover, the training entity may be or may comprise a training apparatus, wherein the apparatus is at least one of an exoskeleton, a robot, a treadmill, a cycling machine and/or a body weight support system. In particular, the trainer of the patient and/or subject may be equipped with at least one sensor or more sensors.

The controller may be configured and arranged for tracking and estimating the training entity movement and for translating it into stimulation data, based on the estimated movement, being provided by the stimulation system to the patient for the patient training for movement reconstruction and/or restoration.

In particular, the controller is a body-worn platform to execute the control software. The controller processes data that is acquired among others from the sensor, the stimulation system, and the programmer, and programs the stimulation system to deliver the correct stimulation.

Furthermore, the controller may be configured and arranged that the tracking and estimating of the movement is performed online and/or offline.

Online tracking and estimating helps to realize a direct transfer of the training entity movement and for translating it into stimulation data being provided by the stimulation system to the patient for the patient training for movement reconstruction and/or restoration. It is helpful to realize a real-time solution and a real-time data transfer.

Here, real-time is defined as an end-to-end latency that is less than 100 ms, preferably less than 50 ms.

Offline configuration by doing the tracking and estimating process offline may allow the controller to program the stimulation system based on recorded sensor data for a period of time of minimum one complete movement, e.g. gait cycle. Performing the tracking and estimating offline may allow to use criteria that could not be used on real-time.

The movement model may be created so that the movement phase takes always the same value at the same event. Using robust criteria that is common to all kind of healthy or pathological movement, this may allow to determine different movement events offline on recorded data.

At the beginning of a rehabilitation session, the movement model used is a general movement model trained on a set of different subjects, the movement model, e.g. gait model is thus not perfect but sufficient to make some steps. Everything is recorded in parallel of the analysis in a sensor buffer. As soon as a whole movement cycle, e.g. gait cycle, is detected, an online expert system determines the past movement event, e.g. gait event, and the movement model is trained to adapt to the new data. Then the movement model used online is updated.

It may be possible to stop the learning process when the movement model is good enough and to store it for further sessions with the same patient.

Onsite tracking and estimating of a patient's movement may allow tracking and estimating the patient him or herself. Remote tracking and estimating of the movement may allow that the movements of a training entity and/or patient and/or physiotherapist are copied to more patients at the same time.

In particular, the controller may allow that tracking and estimating is performed from one patient to another patient. This can be realized for example by transferring the settings from one patient to another patient. In particular, the settings used for one patient can be used for the treatment of another patient. Especially, settings from a healthy person can be used for the treatment of a patient.

In particular, the controller may allow that tracking and estimating is performed and/or transferred from one patient advanced in the rehabilitation process to patients less advanced.

Moreover, the controller may be configured and arranged that the tracking and estimating is performed online and/or in real-time and/or with time delay.

Apart from applying the correct electrical field at the right location, the stimulation needs to be applied at the correct moments in time and correctly sequenced. It may be very helpful for the patient equipped with the system to have stimulation at the moment or close to the moment needed to proceed e.g. with the desired movement. The patient needs to be able to predict when the stimulation will occur in order to make the best use of the stimulation. Likewise, suppressing motion while stimulation is provided also requires that the patient knows when to expect the stimulation. When the stimulation is not synchronized to the patient's (intended) motion, the patient is not able to perform a proper movement. This means that the stimulation needs to be predictable by the patient, as the patient needs to synchronize to the stimulation.

In particular, real-time may be understood in a way that the delay between sense signals and provided stimulation signals shall be not more than 30 ms (see also WO 2016/0279418 A1). Real-time control in sense of the invention and its preferred embodiments, i.e. especially that the delay between sense signals and provided stimulation signals shall be not more than 30 ms, is beneficial for the open-loop approach and also for closed-loop approach.

There is a delay from neural stimulation (e.g. the spinal cord) to muscle activation. In particular, delay values are differing depending on the type of muscle. The controller may be adapted to this kind of different signal delay.

There may be at least two or more sensors forming a sensor network, wherein at least one of the two or more sensors is connected to the controller.

Using a sensor network of two or more sensors, limb position estimates, e.g. lower limb position estimates can be obtained by double integration of the measured acceleration in combination with drift correction. However, also position estimates of the trunk and/or head can be obtained. In this way, non-real-time reconstruction of limb and/or part of a limb and/or trunk and/or head trajectories may be done up to a few centimeters accuracy for healthy subjects. In particular, movement, e.g. gait phase and cadence may be estimated using two sensors.

In particular, two or more sensors may be placed on one foot and/or another part of a leg, including but not limited to the shank and/or thigh and/or hip and/or other parts of the body including but not limited to the trunk, and/or one or two arms and/or one or two hands and/or another part of an arm and/or the head and/or the neck of the patient to provide a precise description of the movement.

More sensors may display different topologies, including but not limited to star network, body network, chain network. Using more sensors located on a chain, e.g. from hip to foot via upper leg, knee and lower leg the relative positions of all leg joints and therefore, the complete kinematics of the lower body, including foot trajectories, but also knee and hip angles may be reconstructed. In general, more sensors can be located on a chain from head to toes to determine body kinematics.

The relative position estimates may be drift-free.

The control system may further comprise an augmented and/or virtual reality module, which is configured and arranged to provide information related to movement reconstruction and/or restoration, especially information related to the training to be performed or being performed for movement reconstruction and/or restoration.

By simulating real-life activities, the patient may be able to perform rehabilitation training in a setting that is usually impossible to create in a hospital environment.

In particular, the augmented and/or virtual reality module may be designed to aid the rehabilitation process and track the patient's progress. The augmented and/or virtual reality module may improve e.g. coordination, balance, muscle strength, range of motion, reaction times, memory.

Augmented and/or virtual reality modules may use different technologies including virtual reality headsets (including e.g. gyroscopes, accelerometers, structured light systems, eye tracking sensors, etc.), eyeglasses, head-up displays, bionic contact lenses, virtual retinal display, head-mounted display, EyeTrap, handheld displays, spatial augmented reality, etc.

Moreover, the augmented and/or virtual reality module may be configured and arranged to provide gamification information related to movement reconstruction and/or restoration.

In particular, the patient's body movements may be transferred to the game world during a rehabilitation session.

In specific cases, this feature may motivate and affect positively the progress of regaining by a patient control of his or her body and/or parts of his or her body, e.g. the limbs. Syncing the physical body in all its expressive capacity with e.g. a digital avatar may allow the patient to analyze his/her movement in a respective training environment.

At least one sensor may be or may comprise at least one of an inertial measurement unit (IMU), an optical sensor, a camera, a piezo element, a velocity sensor, an accelerometer, a magnetic sensor, a torque sensor, a pressure sensor, a displacement sensor, a contact sensor, a EMG measurement unit, a goniometer, a hall sensor and/or a gyroscope and/or motion tracking video camera, or infra-red camera.

Some sensors may require fixed base station in the environment, including but not limited to magnet sensors or infra-red sensors.

Electromagnetic position sensors, optical sensors and cameras may estimate 3D position and orientation.

In particular, magnetic sensors and magnetic field sensors may be incorporated in shoes for walking on a magnetic sensor plate or inserted in the treadmill or gait phase detection device. The magnetic force may be detected and acquired by magnetic sensors under gait training.

Torque sensors may be placed on a bicycle crank for assessing the torque during cycling.

Some sensors may be worn by the patient without acquiring fixed base station, including but not limited to piezo elements, pressure sensors and/or torque sensors.

Velocity sensors may monitor linear and angular velocity and detect motion. 3D angular velocity may be estimated by 3-axis gyroscope.

Said IMU may measure and report 3D accelerations, 3D angular velocities and 3D orientation using a combination of one or more of an accelerometer, one or more of gyroscopes, and optionally one or more of a magnetometer. Optionally, a temperature sensor may also be included to compensate for the effect of temperature on sensor readings. By integrating the angular velocity assessed by said one or more gyroscopes and fusing with data from said one or more accelerometers (Kalman filter), it may be possible to get a precise measurement of the movement and/or angle of e.g. the shank, thigh, foot, arm, and/or hand and/or trunk and/or head. This movement and/or angle may have a regular and characteristic pattern for healthy subjects but not for an injured patient. Based on these measurements the orientation of the IMU with respect to the fixed world can be estimated accurately, using standard sensor fusion algorithms.

To estimate the movement, e.g. gait phase, the (lower) body kinematics need to be determined. The sensors collect motion data, based on which the movement phase, e.g. gait phase or pedal phase is determined in real-time. This can be done directly by attaching sensors to the training entity and/or by the sensor being part of a training entity, or indirectly by measuring muscle activation or by measuring the interaction between the body and/or parts of the body and its/their surroundings and/or by attaching sensors to the body of the patient (e.g. to the head and/or the neck and/or the trunk and/or one or more limbs and/or one or more parts of the limbs). So, the sensor enables to determine movement events, e.g. gait events with criteria that are common to all kind of healthy or pathological gait.

The acceleration and orientation of the body and/or part of the body, e.g. the hip, thigh, shank, foot, arm, hand, trunk, head may be sampled at a sufficiently high rate and sufficiently low latency, such that the sampled acceleration and orientation known to the system closely may match the true acceleration and orientation of the feet.

In some embodiments, the sensor setup may work everywhere in daily life, not bound to a specific location (like when using cameras), and may be independent from assistive devices (e.g., body weight support system, walker, crutches, etc.).

Using a pressure or contact sensor may allow to directly measure the essence of stance which is the weight-bearing phase of gait cycle.

An EMG measurement unit may sense muscle activity by means of surface or intramuscular EMG electrodes for flexors and extensors.

By means of variables like kinematic markers the kinematic of the patient may be sensed directly or indirectly.

Sensors may be worn on the legs and/or feet and/or the trunk and/or the head and/or the arms in case of closed-loop walking, or a single sensor is attached to the bicycle crank or to one or both feet of the patient in case of closed-loop cycling.

Thus, for closed-loop cycling, the stimulation may be determined by the crank angle and/or foot angle.

Pressure sensors and piezo elements may sense food sole pressure distribution, applied force on the ground and applied torque on bicycle crank during stance phase. Swing and stance phase may be estimated, as well as e.g. foot strike heel-off, toe-off, and applied force.

Moreover, the training entity may be the patient himself or herself

In general, it may be possible that the controller is integrated into the stimulation system. Further, it may be possible that the programmer is integrated in the controller or vice versa.

Furthermore, the control system may comprise a pre-warning module, which is configured and arranged to provide a pre-warning signal indicative of providing an upcoming stimulation event.

Regulating the gait to a predefined reference interferes with voluntary motion of the patient. In particular, voluntary motion of the patient may have a large effect on the movement, as the patients voluntary control may modulate muscle activation. The movement pattern may therefore differ from comparable to a healthy subject, to impaired or reduced despite identical stimulation. The pre-warning signal may help the patient to adjust voluntary control to the respective movement planed, thus a regular movement may be performed. The pre-warning signal may be e.g. an audio and/or visual and/or sensory and or haptic signal. The pre-warning signal may include but is not limited to a sound signal, vibration, light signal, smell, taste, pain, temperature (warm, cold), humidity, drought or the like.

In particular, the pre-warning signal may act in a sub-motor threshold region at which a sensation is evoked, but not a motor response.

In the following it is identified which control output parameters exist and their effects on the afferent nerves, as well as their end effects on muscle activation is described. Based on this, it may be selected which output parameters will be controlled by the control system.

BRIEF DESCRIPTION OF THE FIGURES

Further details and advantages of the present invention shall now be disclosed in connection with the drawings.

It is shown in

FIG. 1 a schematic, very simplified representation of a stimulation pulse delivered by a system according to the present invention;

FIG. 3 a table specifying the fiber types, diameter, and function;

FIG. 5 a table specifying the intended movement and the involved agonist muscle and the involved antagonist muscle;

FIG. 6 discrete sets of functional muscle blocks (FMB) and custom muscle blocks (CMB);

DETAILED DESCRIPTION

Note that in the following we primarily refer to CNS/EES stimulation. The one skilled in the art may transfer the stimulation parameters to PNS/FES stimulation.

The control system may provide stimulation data for movement reconstruction and/or restoration for stimulation of afferent nerve fibers using electrical current pulses. Given this starting point, the following stimulation parameters may be identified:

Electrode configuration (which electrodes to use, polarity)
Stimulation (Pulse) amplitude
Stimulation (Pulse) width
Stimulation (Pulse) frequency FIG. 1 illustrates a schematic, very simplified representation of the stimulation pulse, which illustrates the pulse amplitude, pulse width, and pulse frequency. Each stimulation pulse is followed by a neutralization pulse or a neutralization period (not depicted) to remove the electric charge from the tissue in order to avoid tissue damage.

The effects of each of the stimulation parameters are described below.

Electrode configuration: Stimulating a specific muscle group requires applying a specific electrical field at a specific location on the spinal cord or directly through stimulation of motorfibers (neuro-muscular stimulation), or through a limited set reflexes or by transcutaneously stimulating peripheral nerves. Therefore, in the present control system the electrical stimulation may be delivered e.g. to the spinal cord by a lead with multiple electrodes. The location, shape, and direction of the electrical field that is produced may be changed by choosing a different electrode configuration (which electrodes are used, with which polarity and potential) that is used to deliver the current. Hence, the electrode configuration may determine e.g. to which spinal roots the stimulation is delivered, and therefore which subsequent muscles or muscle groups activity will be reinforced.

Figure 2A:
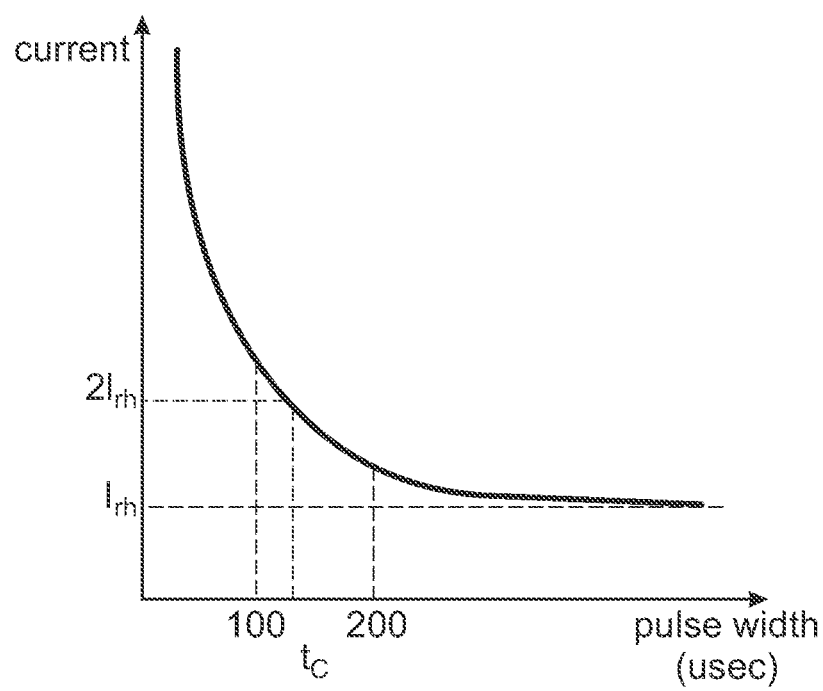
FIG. 2A, B the necessary current and necessary charge to trigger an action potential in a nerve fiber as a function of the pulse width (using a square pulse)
Figure 2B:
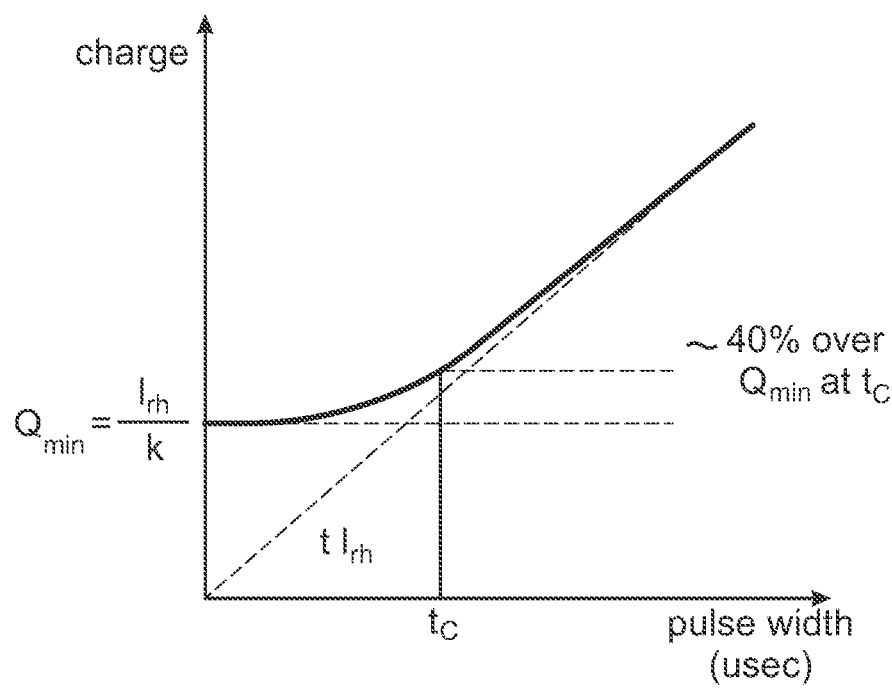

Pulse amplitude and pulse width: In FIG. 2A and FIG. 2B the necessary current and necessary charge to trigger an action potential in a nerve fiber are shown as a function of the pulse width (using a square pulse) (cf: Merrill D R., et al. *Electrical Stimulation of excitable tissue: design of efficacious and safe protocols, J Neurosci methods* 141(2): 171-98 (2005)). FIG. 2A and FIG. 2B also show the rheobase current $I_{rh}$, which is the current that is required when using infinitely long pulse widths, and the chronaxie time $t_c$, which is the required pulse width at a current of $2I_{rh}$.

Although larger currents may be required at smaller pulse widths, the total required charge may decrease with decreasing pulse width, see FIG. 2B. Hence shorter pulses with higher current amplitudes may be energetically beneficial.

For smaller diameter nerves, the current-pulse width curve of FIG. 2A shifts, as smaller diameter fibers may require higher currents. Hence, a higher current may activate more nerve fibers, as also smaller diameter nerve fibers may be activated (until saturation). However, also cross-talk is increased as also more neurons from neighboring roots may be activated. Fortunately, the afferent fibers involved in motor control (fiber types Ia and Ib) may be all relatively large (12-20 μm), while the fibers involved in touch, temperature, and pain feedback (which should not be triggered) may be relatively small (0.5-12 μm), as depicted in FIG. 3. Hence, with increasing pulse width and/or current amplitude, the type Ia and Ib fibers may be the first to be recruited. This may enable recruiting (most of) the relevant fibers while keeping cross-talk and patient discomfort to a minimum.

Pulse frequency: The pulse frequency may determine the frequency of the action potentials generated in the afferent nerves, assuming sufficient charge is delivered each pulse to trigger the action potentials. As no new action potential can occur in a nerve during the refractory period, the frequency of the triggered action potentials will saturate at high pulse frequencies. This saturation point is generally at around 200 Hz for afferent fibers (Miller J P., et al., *Parameters of Spinal Cord Stimulation and Their Role in Electrical Charge Delivery: A Review. Neuromodulation: Technology at the Neural Interface* 19, 373-384, (2016)). However, stimulation at frequencies above the saturation point may still be beneficial, as by increasing frequency the total charge delivered per unit time (i.e. charge per second) can be increased without changing current amplitude or pulse width (Miller J P., et al., *Parameters of Spinal Cord Stimulation and Their Role in Electrical Charge Delivery: A Review. Neuromodulation: Technology at the Neural Interface* 19, 373-384, (2016)).

Pulse positioning: Many tasks, including walking, require simultaneous activation of multiple muscle groups. Hence, to support these tasks, multiple muscle groups may need to be stimulated simultaneously, each requiring a specific electrical field and pulse frequency. When applied simultaneously, these different electrical fields may interact with each other, potentially leading to unintended and uncontrolled effects. Therefore, to avoid this situation, care should be taken that the individual stimulation pulses and their neutralization periods targeting different muscle groups are not applied simultaneously. This may not be considered a stimulation parameter but does identify a required system feature: a pulse positioning algorithm.

The previous section describes the effect of the stimulation parameters on triggering action potentials in afferent nerve fibers. Although triggering these action potentials is an essential step in the therapy, in the end the stimulation should enable or support the patient in performing specific lower body motions, which may require the activation of specific muscles or muscle groups. The effect of the triggered action potentials in afferent nerve fibers on muscle activation may be filtered inside the spinal cord through spinal reflex circuits and modulated through the voluntary control of the patient. Hence, the effect of the stimulation parameters on muscle activation may be not perfectly clear and may be affected by intra- and inter-Patient variations. The following aspects may be of relevance here:

Different patients may have different levels of voluntary control over their lower body, depending on the type and severity of their SCI lesion level and state of (spontaneous) recovery.

Stimulation of afferent nerve fibers may assist or enable activation of the corresponding muscles but may not necessarily enforce motion. The patient may modulate the activation (e.g. make a large or small step without changing the stimulation), or even resist motion of the leg completely. This may vary per patient and may change with increasing recovery.

Conjecture: Because the spinal cord floats in the cerebrospinal fluid, the distance between the spinal cord and the lead electrodes may vary (mostly as a function of the patient's posture: prone—large distance, supine—small distance). Another hypothesis may be that due to posture changes, the layer thickness of low conductive epidural fat between the lead electrodes and the dura/cerebrospinal fluid a changing, leading to an impedance change as seen by the electrodes, and resulting in an altered current/voltage delivered stimulation by the electronics. As a result, the effect of the applied stimulation (including muscle onset and saturation) may also vary with the patient's posture. Although this conjecture is not proven, patients may successfully make use of the described effects to modulate the stimulation intensity by varying their posture: bending forward reduces the intensity, bending backward increases it.

Pulse frequencies between 40 and 120 Hz may mostly be used, although it may theoretically be possible to stimulate up to 500 Hz as this may have benefits for selectivity in muscle activation and improved voluntary control of the patient.

It may be possible that generally increasing the pulse amplitude may not lead to increased recruitment of muscle fibers (with corresponding increased cross-talk), and that increasing the stimulation frequency may lead to increased muscle activation without affecting cross-talk. However, increasing the stimulation frequency may reduce the intensity of natural proprioception and result in a decreased feeling in the leg of the patient. This is probably due to the collision of natural sensory inputs with antidromic action potentials generated by the electrical stimulation. At high frequency (above 100 Hz), patients may even report a complete loss of sensation of the leg and "feel like walking with their legs being absent". This is a non-comfortable situation requiring the patient to make a leap of faith at each single step, believing that the leg that he/she does not feel anymore will support him/her during the next stance phase. Adjusting the balance between stimulation amplitude and frequency may therefore be necessary to find the optimal compromise between cross-talk limitation and loss of sensation. Simulations suggest that a possible workaround may be to shift the stimulation domain to lower amplitudes and even higher frequency, such that with a minimal number of stimulated fibers the same amount of activity is triggered in the spinal cord. Such hypothesis requires validation via additional clinical data. Finally, it may also be identified that different patients require different stimulation, i.e. that the optimal frequency and amplitude settings may vary highly between patients. Hence, the relation between stimulation amplitude and frequency on muscle activation may be still for a large part unclear. Moreover, the optimal stimulation settings may vary during the day, the assistive device that is used (crutches, walker, etc.), over time with improved recovery, and with the goal of the training or activity.

Timing: Apart from applying the correct electrical field at the right location on the spinal cord, they also may need to be applied at the correct moments in time and correctly sequenced. The relevant timing aspects that are identified are listed below.

Figure 4:
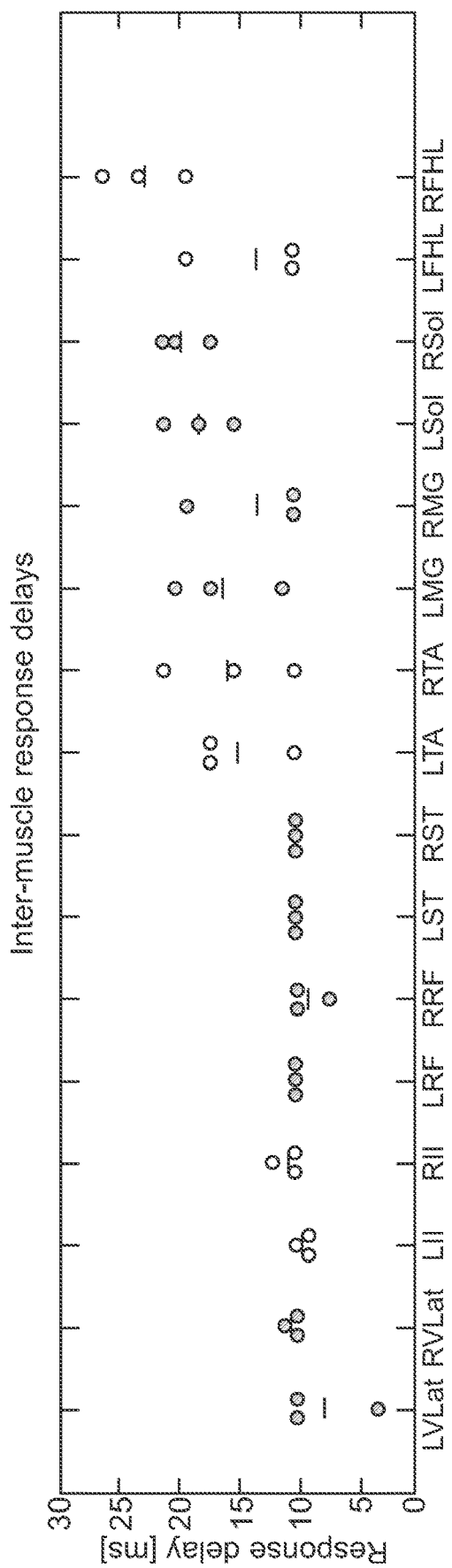
FIG. 4 the relationship between response delay and inter-muscle response delays.

There is a delay from stimulation on the spinal cord to muscle activation (typical values in the order of 0-30 ms depending on the muscle, see FIG. 4, LVLat=left vastus lateralis, RVLat=right vastus lateralis, Lll=left iliopsoas, Rll=right iliopsoas, LRF=left rectus femoris, RRF=right rectus femoris, LST=left semitendinosus, RST=right semitendinosus, LTA=left tibialis anterior, RTA=right tibialis anterior, LMG=left medial gastrocnemius, RMG=right medial gastrocnemius, LSol=left soleus, RSol=right soleus, LFHL=left flexor halluces longus, RFHL=right flexor halluces longus).

While EES enables patients to perform motions, the patient may need to be able to predict when the stimulation will occur in order to make the best use of the stimulation. Likewise, suppressing motion while stimulation is provided also requires that the patient knows when to expect the stimulation. Hence, predictability of the stimulation timing is essential.

When the stimulation is not synchronized to the patient's (intended) motion, the patient may not be able to perform a proper movement. Here, this may mean that the stimulation needs to be predictable by the patient, as the patient needs to synchronize to the stimulation.

The duration of the stimulation for leg swing during walking may need to be finely tuned. For some patients, increasing the duration of this stimulation by 100 ms made the patient jump instead of performing a proper step.

20 ms may be a sufficient resolution for tuning the stimulation timings (i.e. the on/off times of the stimulation for a specific muscle group may not need to be controlled at a precision below 20 ms). Given current data availability, controlling the timings at resolutions below 20 ms may not seem to improve the effectiveness of the stimulation.

Based on the previous sections, the stimulation parameters may be selected in the control system. This may determine the control output space that is used, and therefore the complexity of the control problem and the potential effectiveness of the control system.

First it is discussed which parameter spaces can be reduced or eliminated. The remaining control output space is summarized below.

Electrode configuration: Walking, as well as other movements of the lower extremities, may be composed of well-coordinated flexion and extension of lower body joints by contraction of agonist muscles and relaxation of antagonist muscles. The specific set of agonist and antagonist muscles for joint specific flexion and extension may be grouped, and as the number of joints is limited, this means that only a small discrete set of muscle groups may be needed to be stimulated. For each joint flexion and extension, a Space Time Programmer (STP for programming space and time of stimulation) will support creating the optimal electrode configuration for activation of the agonist muscles while avoiding activation of the antagonist muscles (as well as avoiding activation of muscles on the contralateral side). This may be done in a procedure called the functional mapping. We define the Functional Muscle Blocks (FMB), as the resulting stimulation configurations for each specific muscle group. At least 12 specific FMBs have been identified for use the control system, these are listed in FIG. 5 with their corresponding agonists and antagonists.

As knee flexion and hip extension both involve the semitendinosus, it is physically not possible to target knee flexion and hip extension separately. Therefore, FIG. 5 does not include knee flexion (this could be considered redundant to hip extension).

Next to the 12 FMB listed in FIG. 5, it is also envisioned that the trainer/therapist/physiotherapist may create Custom Muscle Blocks (CMB). Creating CMB may be useful in case the trainer/therapist/physiotherapist wants to apply stimulation that does not specifically target any of the 12 muscle groups targeted by the FMB, or in case the trainer/therapist/physiotherapist wants to use a variant of one of the 12 FMB in a specific task.

Hence, by limiting the electrode configurations to the discrete set of FMB and CMB (versus an infinite number of possible electrode configurations), the control problem complexity may be reduced considerably without significantly affecting the potential effectiveness of the control system. Stimulation for a Task is then reduced to stimulation of (a subset of) the predefined FMB and CMB, see FIG. 6. For this example, the Right Trunk Stability is used in both Task 1 and Task 2.

The functional mapping procedure may require measuring the response of each of the muscles listed in FIG. 5 with EMG sensors. Due to the large number of muscles, this requires attaching many EMG sensors to the patient (which is time consuming) and processing a large amount of data.

Moreover, as motion of the patient may induce signal artifacts, the functional mapping may be best performed while the patient is not moving. For these reasons, the functional mapping procedure may be performed in a separate session using a STP for programming space and time of stimulation, and not e.g. adaptively within the control system. Hence, the configuration of FMB and CMB may be considered as a given to the control system.

Pulse width: From the viewpoint of triggering action potentials in afferent nerve fibers, the parameters pulse width and pulse amplitude may be tightly linked and may together determine which afferent nerve fibers are recruited. Increasing the pulse width may allow to reduce the amplitudes and decreasing the pulse width may allow reducing energy consumption (as the total required charge for triggering an action potential decreases with decreasing pulse width, see FIG. 2B) and stimulating more FMB simultaneously or at higher frequencies. However, from a control perspective the two parameters may be (almost) redundant, as increasing either parameter may lead to the recruitment of more afferent nerve fibers over a larger area.

Pulse widths below chronaxie time $t_c$ may quickly require high currents (and thus high voltages), which is difficult to produce and may lead to patient discomfort. Beyond $t_c$, the strength-duration curve of FIG. 2A is almost flat, so increasing pulse width beyond $t_c$ has little effect on the required amplitudes while it increases total power consumption. Also considering that having a fixed pulse width simplifies the pulse positioning, the pulse width is chosen to be fixed (at a value near chronaxie time $t_c$ such that both energy consumption and required current amplitudes remain low, where $t_c \approx 200$ µs for afferent dorsal root nerve fibers in humans). This reduces the complexity of the control problem by reducing the number of output parameters.

This may leave the following stimulation parameters to be controlled over time by the control system:

Which FMBs to stimulate

Stimulation amplitude per FMB

Stimulation frequency per FMB

The pulse positioning may be considered a lower level problem and may therefore be not a direct output of the control system (system feature). The pulse positioning will be performed by the IPG.

Although combining amplitude and frequency to a single 'intensity' parameter has been considered, doing so may not be envisioned for the control system, as these parameters may have very different effects. On triggering action potentials in afferent nerve fibers, the amplitude and frequency may be independent parameters: the amplitude determines in which afferent nerve fibers action potentials are triggered, the frequency determines the rate at which they are triggered. Hence, in principle the amplitude determines which muscle fibers are activated, the frequency determines how hard, although it is unclear if the independence of the two parameters also holds for muscle activation due to the signal processing that occurs in the spinal cord. Moreover, it may be apparent that for some patients changing the amplitude gives the best results, while for other patients the frequency may be the more useful parameter.

As the precise relation between frequency and amplitude is not known in the clinical context it may not be recommended to combine frequency and amplitude to single parameter. Hence, the stimulation frequency and amplitude may be controlled independently from each other.

In the following the sensor, the controller, the programmer and the stimulation system (e.g. IPG) of the present invention are described in greater detail.

Sensors: Battery powered, body worn sensors (directly or indirectly, and/or sensors placed on and/or integrated into one or more training entities), collecting motion data, and sending it to the controller. Its intended use is to capture body motion parameters.

Controller: Battery powered, body worn device (directly or indirectly), receiving data from sensor(s) and able to send stimulation commands to the IPG for specific tasks (i.e. an activity/training exercise). Its intended use is to determine optimal stimulation settings for any given task and providing this information to the IPG. In addition, this device can take the IPG out of shelf mode, charge the IPG battery transcutaneous, and initiate an IPG-lead integrity test.

Programmer: The programmer, or also called the clinician programmer, can be used to receive inter alia stimulation parameter, patient data, physiological data, training data etc.

It may comprise a Space Time Programmer (STP) for e.g. programming space and time of the stimulation, a Physiotherapist Programmer (PTP) for e.g. allowing the physiotherapist adjustment to the stimulation, and a patient Programmer (PP) for e.g. allowing the patient to select a specific stimulation program.

The Space Time Programmer (STP), Physiotherapist Programmer (PTP), and Patient Programmer (PP) can be embodied as applications installed on a mobile device that communicate with the controller. They are used by the treating physician (TP), a physiotherapist (PT), or the Patient to provide inputs to the controller, e.g., selecting, starting, and stopping a task or configuring stimulation parameters.

The programmer can allow adjusting the stimulation parameters of a task, while the task is running. This enables the user to tune the stimulation without having to start and stop the task, which would be very cumbersome at the start of the rehabilitation training, when all stimulation partitures are developed and tuned.

Generally speaking, the programmer may have the following structure:

In a first embodiment, the programmer can be embodied such that it is possible to receive inter alia but not limited to stimulation parameters, patient data and the like, check and/or reprogram the stimulation data and send it back to e.g. the controller.

The programmer is in this first embodiment capable to receive data from the implanted (part of the) system (e.g. the controller), display data, receive input from the user and then send it back to the controller. In other words: The programmer can receive, process and re-send the data.

In a second embodiment, the programmer may receive data from a remote database. The database may be e.g. linked with the stimulation system via a separate interface, which is configured for data transfer from the system to the database only.

The programmer is in this second embodiment capable to receive data from the remote database, display data, receive input from the user and then send it to the controller. In other words: The programmer is only in connection with the controller for sending data, it does not receive data from the controller or any implanted system parts.

Stimulation system, here IPG: Implantable Pulse Generator. A battery powered device that generates the electrical stimulation, subcutaneously implanted. Its intended use is to deliver electrical stimulation to the lead based on command received from the controller.

Figure 7:
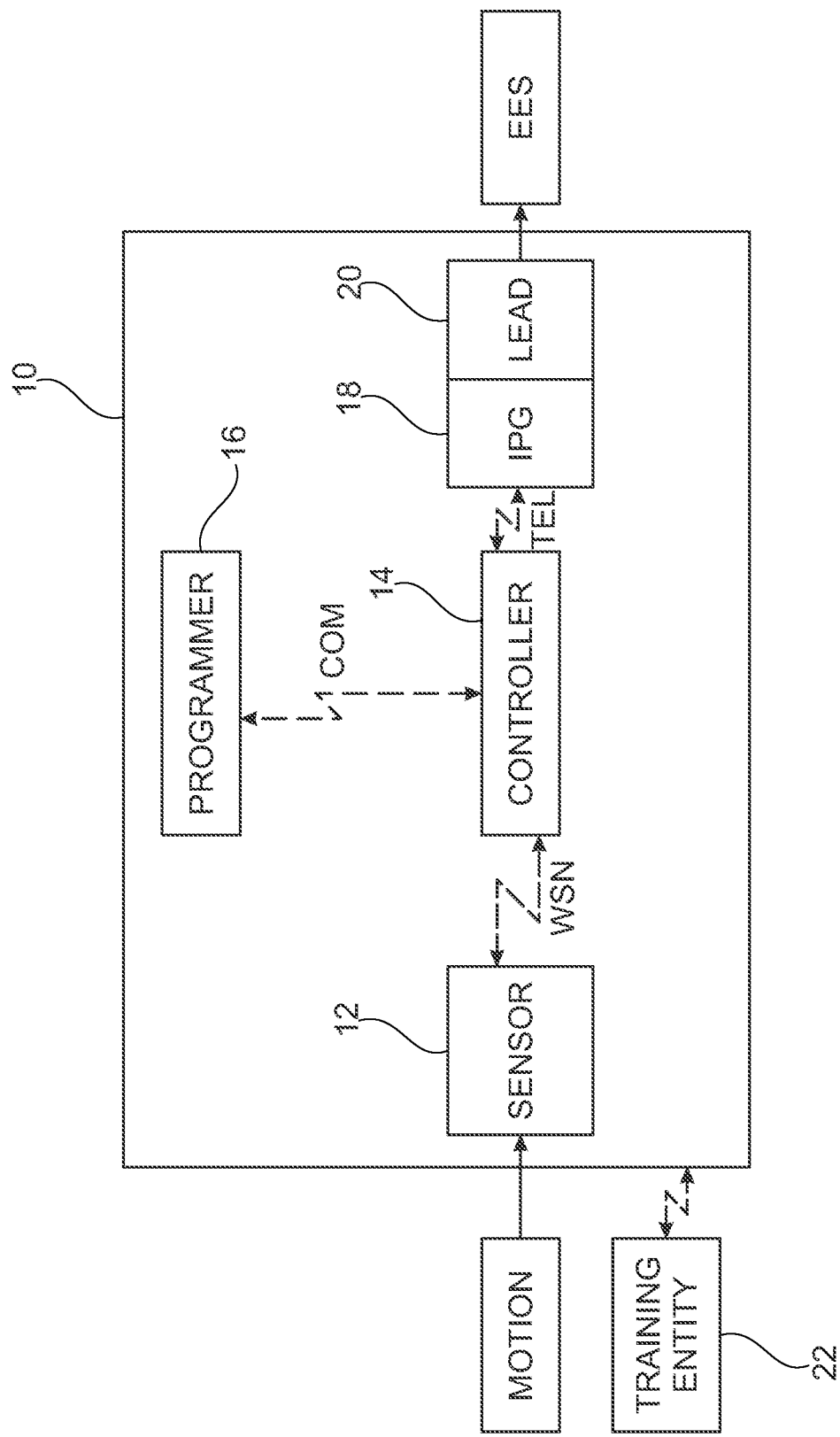
FIG. 7 a general layout of an embodiment of a control system for a movement reconstruction and/or restoration system for a patient according to the present invention.

FIG. 7 shows a general layout of an embodiment of the control system 10 for a movement reconstruction and/or restoration system for a patient P according to the present invention.

The control system 10 comprises one or more sensors 12, while two or more sensors could form a sensor network.

Furthermore, the control system 10 comprises in the shown embodiment a controller 14.

Additionally, the control system 10 comprises a programmer 16.

There is also an implantable pulse generator (IPG) 18.

In an alternative embodiment, the pulse generator can be also a non-implantable pulse generator.

The control system may further comprise a lead 20.

The lead 20 may be a connection cable (i.e. lead cable) with one or more electrodes.

The one and more electrodes may be arranged on a lead paddle connected to the lead.

In one embodiment, the controller 14 is body-worn, the programmer 16 is a mobile device, the IPG 18 is implanted in the body, and the one or more sensors 12 is/are attached to the patient's limbs/feet or to a training entity 22.

The training entity 22 could be a bicycle.

In one embodiment, the training entity 22 could be a trainer T and/or physiotherapist.

The one or more sensors 12 is/are connected to the controller 14.

The connection between the one or more sensors 12 and the controller 14 is a bidirectional connection.

The connection between the one or more sensors 12 and the controller 14 is in the shown embodiment a direct connection.

However, also an indirect connection (i.e. with another component of the control system 10 in between) would be generally possible.

The connection between the one or sensors 12 and the controller 14 is established in the shown embodiment via a wireless network WSN.

However, also a cable-bound connection would be generally possible.

Moreover, the controller 14 is connected to the programmer 16, in the shown embodiment by means of a direct connection COM (also called "communication line").

However, also an indirect connection would be generally possible.

The connection between the controller 14 and the programmer 16 is established in the shown embodiment via a wireless link.

However, also a cable-bound connection would be generally possible.

The controller 14 is connected to the IPG 18 in the shown embodiment via a direct connection.

However, also an indirect connection (i.e. with another component of the control system 10 in between) would be generally possible.

The connection between the controller 14 and the IPG 18 is established in the shown embodiment via a wireless link TEL.

However, also a cable-bound connection would be generally possible.

The IPG 18 is connected to the lead 20.

By means of the one or sensors 12 signals indicative for a motion, e.g. movement of position of a limb, e.g. a foot or hand, or the trunk or the head or other parts of the body can be sensed and used by the control system 10.

The sensor signals are transferred to the controller 14 and there processed.

The controller 14 processes data that is from e.g. the sensor 12, the IPG 18, and the programmer 16.

By means of the controller 14 the control software is executed.

By means of the programmer 16 inputs to the controller 14, e.g., selecting, starting, and stopping a task or configuring stimulation parameters are provided.

It is generally possible that the programmer 16 allows adjusting the stimulation parameters of a task, while the task is running.

It is generally possible that the programmer 16 is used by a therapist, physiotherapist, or patient.

The controller 14 programs the IPG 18 to deliver the correct stimulation via the lead 20.

Via the lead 20 and the respective electrode(s) stimulation can be provided, here EES.

Alternatively, also other suitable stimulation signals may be provided.

In particular, also PNS stimulation could be provided.

In particular PNS stimulation could be provided by an IPG 18.

In general, the control system 10 creates and/or guides a movement model m for a patient and/or adjusts stimulation settings based on sensor 12 input.

However, also an external stimulation system could be generally possible.

Not shown in greater detail in FIG. 7 is the fact that the one or more sensors 12 is/are part of or attached to a training entity 22.

In an alternative embodiment the training entity 22 could also be the patient P himself or herself It is also possible that the controller 14 tracks and/or estimates the movement of the training entity 22 for translating it into stimulation data, based on the estimated movement, being provided by the stimulation system 18 to the patient for the patient training.

Not shown in FIG. 7 is that the control system 10 may comprise a pre-warning module, which is configured and arranged to provide a pre-warning signal indicative of providing an upcoming stimulation event.

In particular, the pre-warning signal may act in a sub-motor threshold region at which a sensation is evoked, but not a motor response.

Not shown in FIG. 7 is that the at least one sensor 12 is an inertial measurement unit (IMU).

In an alternative embodiment, the at least one sensor 12 could also be an optical sensor, a camera, a piezo element, a velocity sensor, an accelerometer, a magnetic field sensor, a torque sensor, a pressure sensor, a displacement sensor, an EMG measurement unit, a goniometer, a magnetic position sensor, a hall sensor, a gyroscope and/or motion tracking video cameras, or infra-red cameras.

Not shown in FIG. 7 is that the control system 10 could further comprise an augmented and/or virtual reality module, which is configured and arranged to provide information related to movement reconstruction and/or restoration, especially information related to the training to be performed or being performed for movement reconstruction and/or restoration.

Further not shown in FIG. 7 is that the augmented and/or virtual reality module could be configured and arranged to provide gamification information related to movement reconstruction and/or restoration.

Further not shown in FIG. 7 is that it could be generally possible that the controller 14 and/or the programmer 16 are integrated into the IPG 18 or vice versa. Further, it could be possible that the programmer 16 is integrated in the controller 14 or vice versa.

In general, every single component of the control system 10 could be integrated in any other component of the control system 10.

According to the state of the art, voluntary control of movement still cannot be achieved by the subject. It is important to keep in mind that the patient is not a robot and can and should not be stimulated and controlled as a robot. Therefore, there is a lack to have a system which overcomes the drawbacks of the prior art. In particular, there is the need of a system stimulating the patient not as a robot. The goal of applying stimulation is not to control the patient, but to support the patient during training and daily life activities.

Hence, the control system 10 shall support the patient's own natural control loop composed of the brain, nervous system, and sensory organs. This means that said control system should not e.g. adjust the stimulation parameters to force the patient's lower body motion to a given reference trajectory. Instead, the patient should be able to determine e.g. the walking cadence.

Figure 8A:
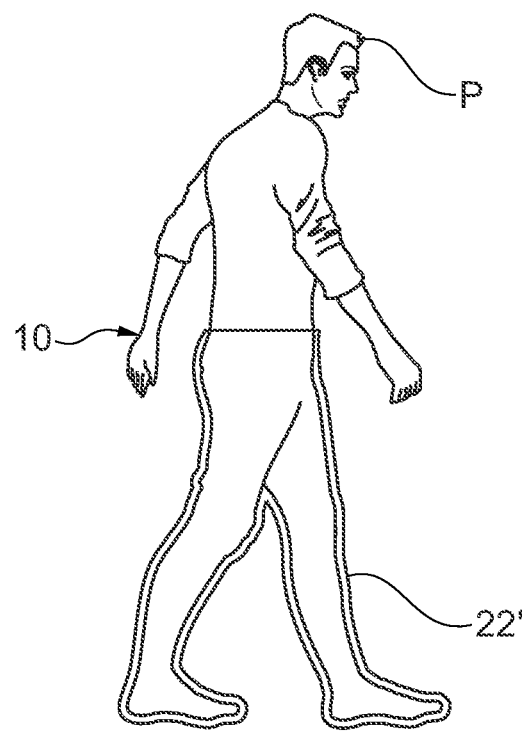
FIG. 8A a schematical drawing of a patient equipped with an exoskeleton in connection with the embodiment disclosed in FIG. 7 according to the present invention.

FIG. 8A shows a patient equipped with an exoskeleton in connection with the embodiment disclosed in FIG. 7 according to the present invention.

In this embodiment, a patient P is equipped with said control system 10 disclosed in FIG. 7 and a training entity 22, in particular an exoskeleton 22a.

The exoskeleton 22a in this embodiment is an external structure designed around the shape and function of the patient's P lower body, particularly the patient's P legs.

However, in an alternative embodiment the exoskeleton 22a could also be designed around the patient's P trunk and/or neck and/or head and/or arms.

In an alternative embodiment, the exoskeleton 22a could also be designed around the total body of the patient P.

The one or more sensor(s) 12 is/are placed on the exoskeleton 22a to assess leg kinematics.

In an alternative embodiment, the sensors 12 could also be integrated in the exoskeleton 22a.

According to FIG. 7, by means of the one or more sensors 12 attached to the exoskeleton 22a signals indicative for a motion, e.g. movement of position of the patient's P body and/or one or more parts of the patient's P body, here a leg and/or a foot, can be sensed and used by the control system 10.

The controller 14 tracks and/or estimates the movement of the exoskeleton 22a and translates it into stimulation data, based on the estimated movement, being provided by the stimulation system 18 to the patient for the patient training.

In an alternative embodiment, remote control of the system and the exoskeleton 22a is possible.

Not shown in greater detail in FIG. 8A is that other embodiments of the training entity 22 could generally comprise a robot, a treadmill, a cycling machine and/or a body weight support system or the like.

Not shown in FIG. 8A is that the training entity 22 could also be the patient P himself or herself.

Figure 8B:
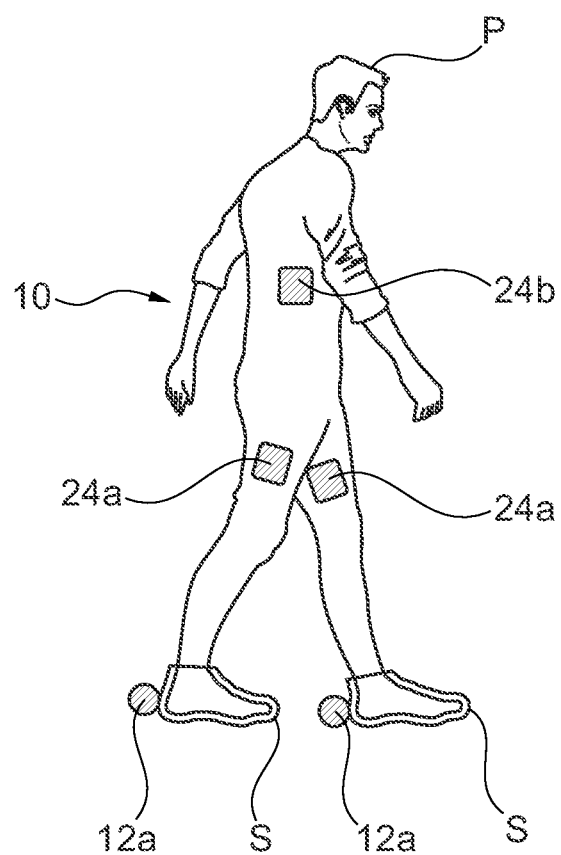
FIG. 8B a perspective view of a patient equipped with the control system disclosed in FIG. 7 comprising two sensors according to the present invention.

FIG. 8B shows a perspective view of a patient P equipped with the control system 10 disclosed in FIG. 7 comprising two sensors 12 according to the present invention.

In this embodiment, a patient P is equipped with said control system 10 disclosed in FIG. 7 comprising two sensors 12, which are here two IMUs 12a attached to the shoes S of the patient P.

In particular, one IMU 12*a* is attached to the left shoe S of the patient P and one IMU 12*a* is attached to the right shoe S of the patient P.

In this embodiment, the IMUs 12*a* are placed on the heel area of the shoes S of the patient P.

In this embodiment, the control system 10 comprises also two electrodes 24*a* for FES.

In particular, one electrode 24*a* for FES is attached to the left leg of the patient P and one electrode 24*a* for FES is attached to the right leg of the patient P.

However, it could be generally possible that each leg of the patient P is equipped with two or more electrodes 24*a* for FES.

In particular, one electrode 24*a* for FES is attached to the left upper leg of the patient P and one electrode 24*a* for FES is attached to the right upper leg of the patient P.

However, it could be generally possible that the one or more electrodes 24*a* for FES are placed at any position(s) of the legs and/or hips and/or trunk of the patient P.

Further, in this embodiment, the control system 10 comprises one electrode 24*b* for EES.

The electrode 24*b* for EES is attached to the dorsal roots of the patient P.

However, also positioning two or more electrodes 24*b* for EES to the dorsal roots, in the epidural space, or on top of the spinal cord could be generally possible.

According to FIG. 7, by means of the two IMUs 12*a* attached to each shoe S of the patient P each movement of the left foot and right foot of the patient P is sensed and used by the control system 10.

The controller 14 tracks and/or estimates the movement of the foot of the patient P for translating it into stimulation data, based on the estimated movement, being provided by the IPG 18 to the patient P.

The IPG 18 provides FES via the lead 20 and the electrode module 24 with the one or more electrodes 24*a*.

The IPG 18 provides EES via the lead 20 and the electrode module 24 with the one or more electrodes 24*b*.

In an alternative embodiment, the IMUs 12*a* could be placed at and/or inserted in, and/or integrated in different positions in the shoe S or in the shoe sole and/or in the shoe insole.

In an alternative embodiment, the control system 10 could comprise only one IMU 12*a* positioned directly or indirectly to the left foot or the right foot, or the left shoe S or the right shoe S of the patient P.

Figure 8C:
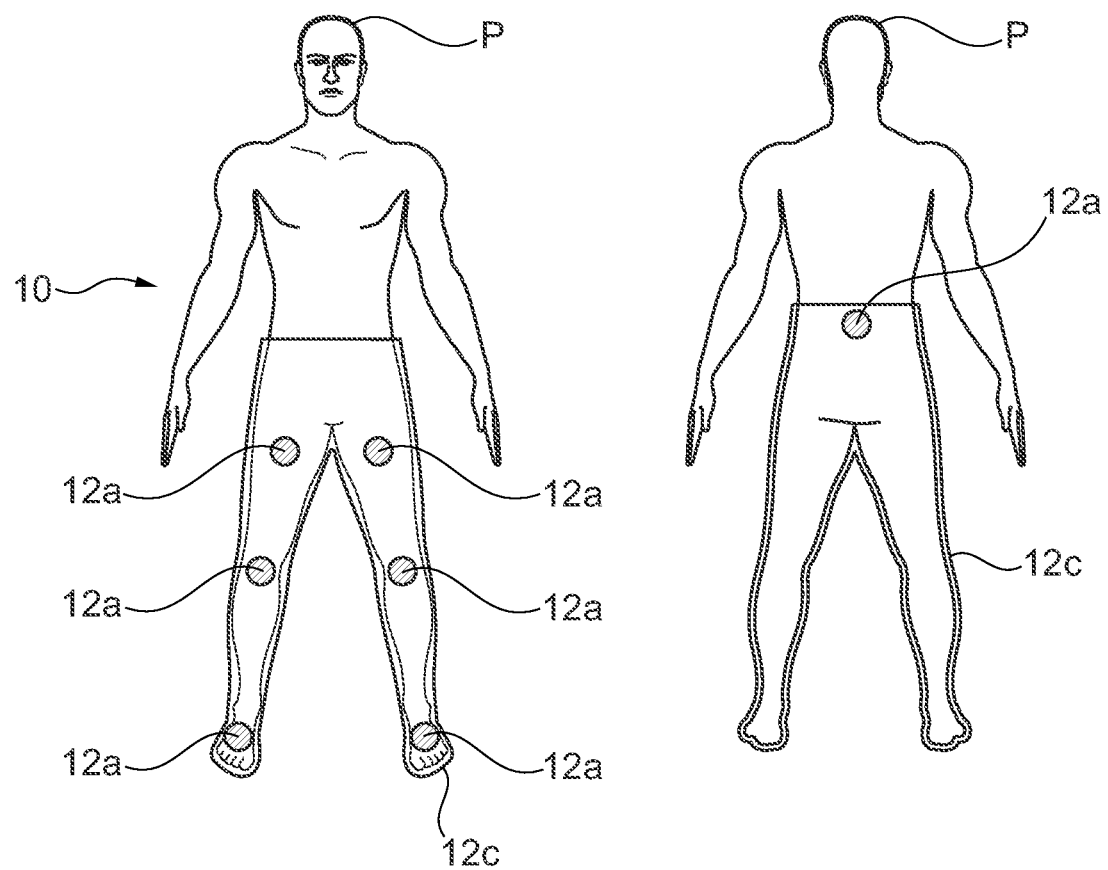
FIG. 8C a perspective view of a patient equipped with the control system disclosed in FIG. 7 comprising seven sensors.

Alternatively, a patient P equipped with the control system 10 disclosed in FIG. 7 could be equipped with two or more sensors 12 for each foot and/or leg, cf. also FIG. 8C.

In particular, a patient equipped with the control system 10 disclosed in FIG. 7 could be equipped with more sensors 12 located on a chain, e.g. from hip to foot via thigh, knee and shank.

In general, two or more sensors 12 can be located on a chain from head to toes.

In particular, a shoe S and/or a shoe sole and/or a shoe insole could be equipped with two or more sensors 12.

Said sensors 12 may be positioned at any place from the distal end to the proximal end of the foot, in particular in the heel area and/or the metatarsal area and/or the toe area, and/or the sides of the feet.

In an alternative embodiment, the one or more sensor(s) 12 could be part of and/or inserted and/or integrated into and/or onto an exoskeleton, tights, a belt, straps, a stretching band, a knee sock, a sock and/or a shoe S of the patient.

However, it could be generally also possible that socks and tights consist of or comprise a piezoelectric textile sensor integrated in the trunk, waist, hip, knee, heel and/or toe area.

An electrical response according to a mechanical stretching, pressing or pulling could be delivered.

In particular, socks or tights could be equipped with electrodes and/or electro conductive yarn.

Alternatively, magnetic sensors and magnetic field sensors could be incorporated in shoes S for walking on a magnetic sensor plate or inserted in the treadmill or gait phase detection device.

The magnetic force could be detected and acquired by magnetic sensors under training, e.g. gait training.

Not shown in FIG. 8B is that for assessing upper body motion and/or arm motion and/or hand motion, the one or more sensors 12 could be inserted and/or integrated into and/or onto clothing or the like for the upper body, the trunk and/or arms, and or hands, including but not limited to a top, a longsleeve, a pullover, a jacket, one or more arm sleeves, gloves, and/or one or more armlets.

Not shown in FIG. 8B is that the electrodes 24*a* for FES could also be configured and arranged for foot and/or leg cramp stimulation to release cramp and/or detection of foot and/or leg cramp.

Not shown in FIG. 8B is that stimulating motion of one or more limbs and/or one or more parts of a limb does not necessarily require stimulating on the locomotor system of one or more limbs and/or one or more parts of the limb, respectively, directly.

As just one example, the spinal cord or the upper leg may be stimulated to induce a reflex and/or motion of the foot.

FIG. 8C shows a perspective view of a patient equipped with the control system 10 disclosed in FIG. 7 comprising seven sensors 12.

In this embodiment, a patient P is equipped with said control system 10 disclosed in FIG. 7 comprising seven sensors 12, which are here seven IMUs 12*a*.

The seven IMUs 12*a* build a sensor network 12*c*.

In this embodiment, the seven IMUs 12*a* are attached to the lower body of the patient P.

In particular, one IMU 12*a* is placed centrally in the hip area, whereas the left leg is equipped with three IMUs 12*a* placed on the foot, the lower leg, and the upper leg, and whereas the right leg is equipped with three IMUs 12*a*, placed on the foot, the lower leg, and the upper leg, respectively.

However, also alternative placements of the IMUs 12*a* along the legs and/or feet and/or the lower body could be generally possible.

In general, also alternative placements of the IMUs 12*a*, or other sensor 12 types, along the body and/or parts of the body, e.g. the head, the neck, the trunk and/or one or both arms and/or one or both hands could be generally possible.

According to FIG. 7, by means of the seven IMUs 12*a* placed on the lower body of the patient P each movement of the legs and feet of the patient P is sensed and used by the control system 10.

According to FIG. 8B, both FES and EES can be provided by the IPG 18, the lead 20 and the electrode module 24 with respective electrodes 24*a* and 24*b*.

Figure 8D:
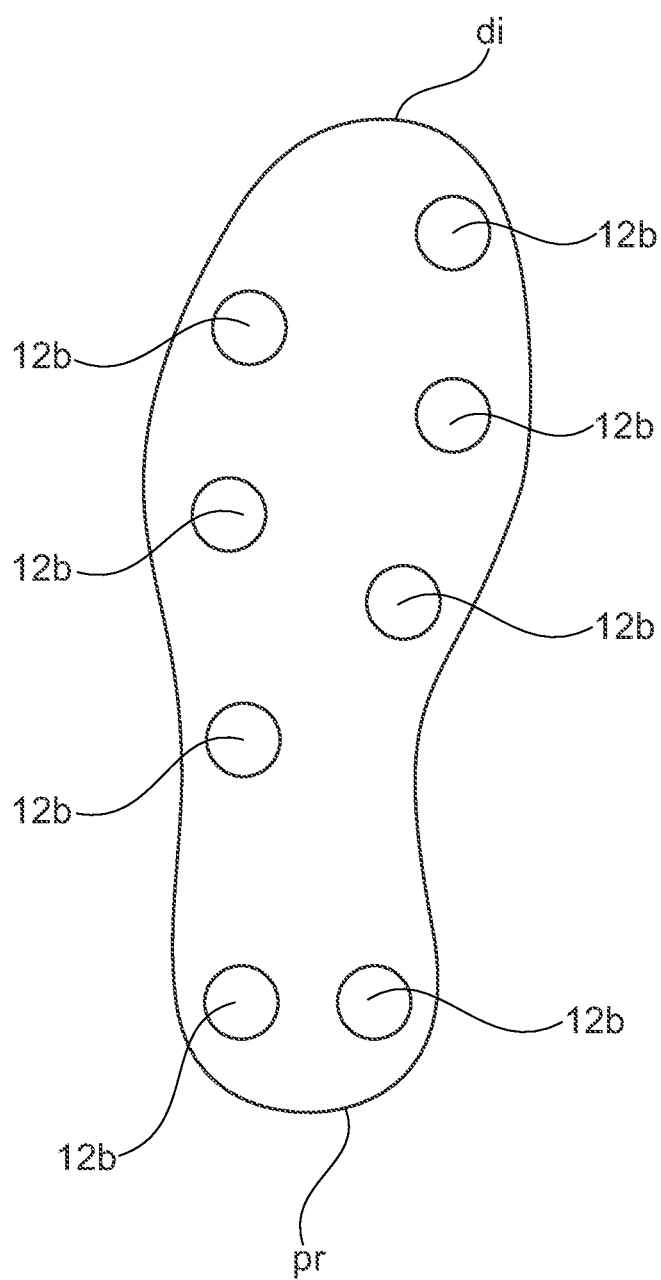
FIG. 8D a perspective view of a sensor insole according to the present invention.

FIG. 8D shows a perspective view of a sensor insole according to the present invention.

In this embodiment, according to the control system 10 disclosed in FIG. 7, various sensors 12 are integrated into a sensor insole 300 of a shoe S of a patient P.

In this embodiment, the sensors 12 are pressure sensors 12b.

In particular, eight pressure sensors 12b are incorporated in a sensor insole 300 of a shoe S of a patient P.

In particular, the eight pressure sensors 12b are distributed from the distal end di of a sensor insole 300 to the proximal end pr of a sensor insole 300 of a shoe S of a patient.

In particular, the eight pressure sensors 12b are distributed along the heel area, the metatarsal area, and the toe area of the sensor insole 300.

In particular, two pressure sensors 12b are placed in the heel area, two pressure sensors 12b are placed in the toe area and four pressure sensors 12b are placed in the metatarsal area of the sensor insole 300.

In general, both shoes S of a patient P could be equipped with sensor insoles 300.

The sensor insoles 300 provide a precise map of the foot force.

In particular, the pressure sensors 12b in the sensor insole 300 provide a precise description of the gait phase and cadence, e.g. pre-swing, swing, loading response and/or stance (or alternatively swing, stance, toe-off, midswing, heel strike, flat foot, midstance and/or heel-off) can be identified for one foot by analyzing sensor data obtained from one sensor insole 300 of a shoe S.

The same events and parameters can be identified for the other foot of the patient P by using a second sensor insole 300.

By combining signals of sensor insoles 300 of both feet of a patient P, together with the gait phase and cadence of the stimulation input, a reliable gait phase and cadence estimate can be provided.

The sensor stream is transmitted to the controller 14 according to the disclosure of FIG. 7.

In one embodiment, alternative placements of the eight pressure sensors 12b in a sensor insole 300 could be possible.

However, it could be also possible that 1-7 or more than 8 pressure sensors 12b are integrated in a sensor insole 300 of a shoe S of a patient P.

It could also be possible that the sensor insole 300 itself is a pressure sensor 12b.

Figure 8E:
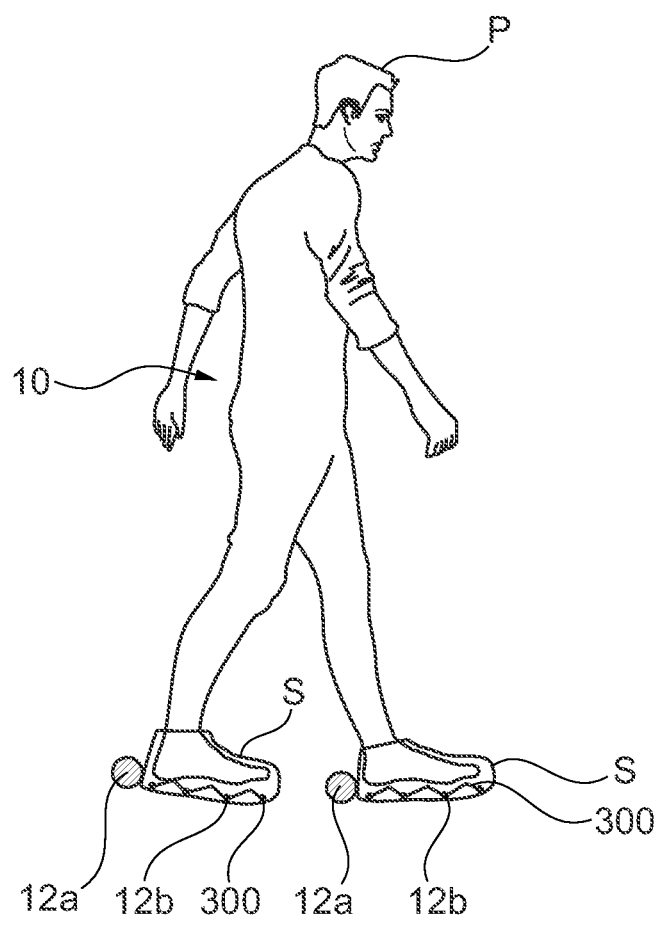
FIG. 8E a perspective view of a patient equipped with the control system disclosed in FIG. 7 comprising one IMU and one pressure insole for each foot according to the present invention.

FIG. 8E shows a perspective view of a patient equipped with the control system disclosed in FIG. 7 comprising one IMU and one pressure insole for each foot of the patient according to the present invention.

In this embodiment, a patient P is equipped with the control system 10 disclosed in FIG. 7 including one IMU 12a placed on the left shoe S and one IMU 12a placed on the right shoe S of a patient P as disclosed in FIG. 8B and one sensor insole 300 as disclosed in FIG. 8D for the left shoe S of the patient P and one sensor insole 300 as disclosed in FIG. 8D for the right shoe of the patient P.0

Accordingly, the sensor insoles 300 for both shoes of the patient P comprise eight pressure sensors 12b (only exemplarily shown in FIG. 8D).

Alternatively, a patient P could be equipped with the control system 10 described in FIG. 7 including one IMU 12a and one respective sensor insole 300 for the left or the right foot.

In another embodiment, the IMU 12a and/or the sensor insole 300 can be replaced by another type of sensor 12 including but not limited to e.g. a piezo element.

In this embodiment, it could be possible that the piezo element is integrated in wearables like e.g. a sock, a knee sock, tights, a shoe.

Figure 9:
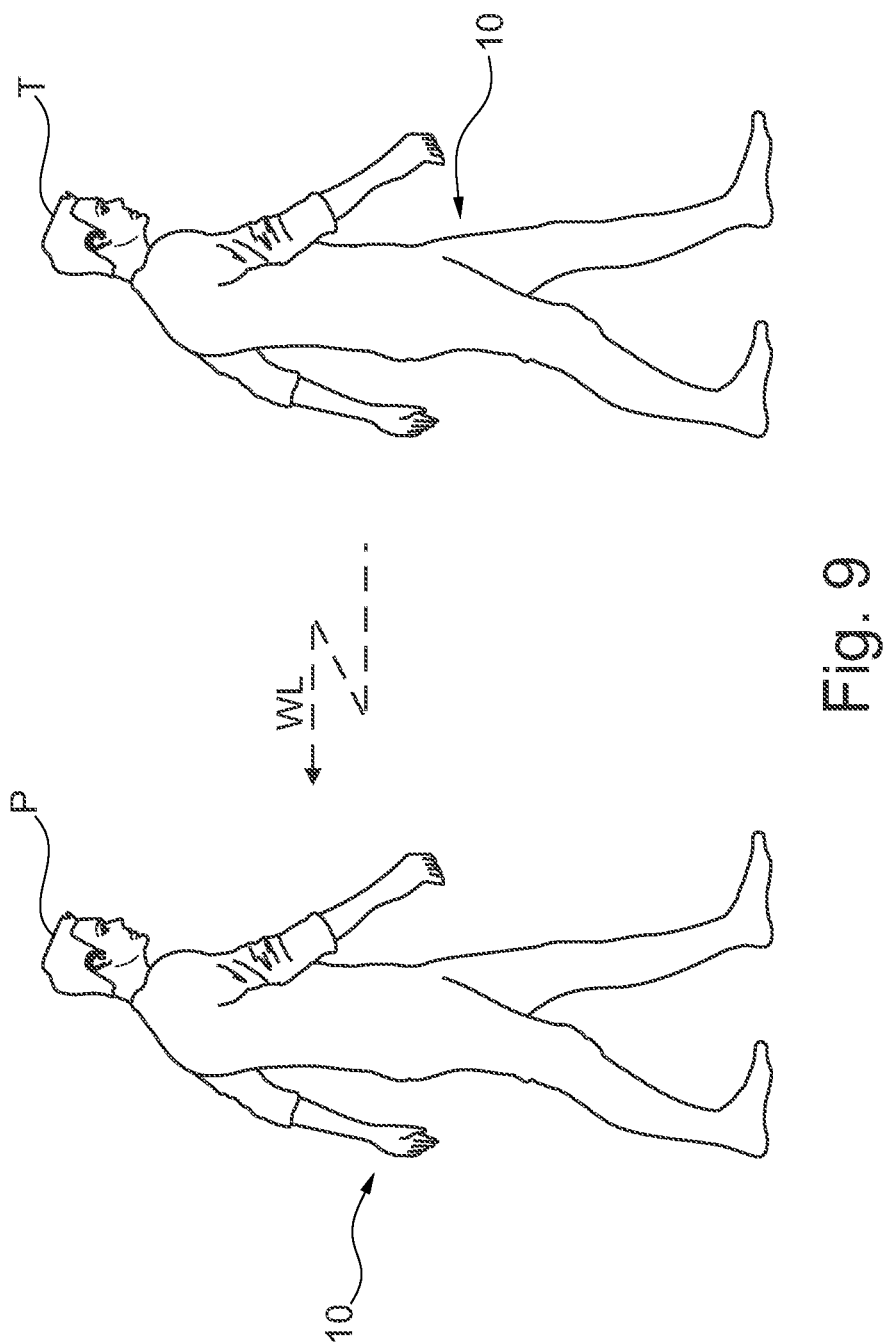
FIG. 9 a schematical view of a patient and a trainer (rehabilitation specialist) according to the present invention.

FIG. 9 shows a schematical view of a patient P and a trainer T (rehabilitation specialist) according to the present invention.

In this embodiment, the patient P and the trainer T are each equipped with one control system 10 disclosed in FIG. 7.

In this embodiment, the control system 10 of the patient P and the control system 10 of a trainer T are interconnected.

The connection between the control system 10 of the patient P and the control system 10 of the trainer T is established by a wireless link WL.

However, also a cable-bound connection would be generally possible.

By means of a wireless link WL between the control system 10 of the patient P and the control system 10 of the trainer T reference data from the control system 10 of the trainer T are copied to the control system 10 of the patient P.

In particular, by means of a wireless link WL between the control system 10 of the patient P and the control system 10 of the trainer T the timing of stimulation of patient P is synchronized to the motion(s) of trainer T.

However, also other reference data, including but not limited to step high or step size could generally be transferred from the control system 10 of the trainer T to the control system 10 of the patient P.

In particular, the control system 10 of the trainer T functions as reference for open-loop stimulation of the patient P by the control system 10 of patient P.

Alternatively, the control system 10 of trainer T could function as reference for closed-loop stimulation of the patient P by the control system 10 of patient P.

Note that different gait events (toe-off, midswing, heel strike, flat foot, midstance and/or heel-off, or alternatively pre-swing, swing, loading response and/or stance) can be synchronized between the trainer T and the patient P.

However, also for movements other than gait, e.g. cycling, swimming, rowing, standing up, sitting down, different movement events can be synchronized between the trainer T and the patient P However, in an alternative embodiment it could be generally possible that data are transferred offline and with time-delay.

Note that said synchronization could enable identifying and/or evaluating and/or correcting for the difference(s) between the healthy, regular and physiological movement of the trainer T and the impaired and irregular movement of the patient P.

Further, synchronizing a control system 10 of a patient P more advanced in the rehabilitation process to the control system 10 of a patient P less advanced in the rehabilitation process would be generally possible.

However, also partially or totally tracking and estimating control algorithms and/or movement model from the control system 10 of the patient P to the control system 10 of the trainer T is generally possible.

Further, also synchronizing and/or partially or totally tracking and estimating control algorithms and/or movement model from a control system 10 of a patient P more advanced in the rehabilitation process to the control system 10 of a patient P less advanced in the rehabilitation process would be generally possible.

The tracking and estimating could be performed online and/or in real-time and/or with time delay.

However, in an alternative embodiment also tracking and estimating offline could be generally possible.

Not shown in FIG. 9 is the fact that the patient P, the trainer T or the one or more further patients could be equipped with a training apparatus, e.g. an exoskeleton 22a, a robot, a treadmill, a cycling machine and/or a body weight support system or the like, as disclosed in FIG. 8A.

Figure 10:
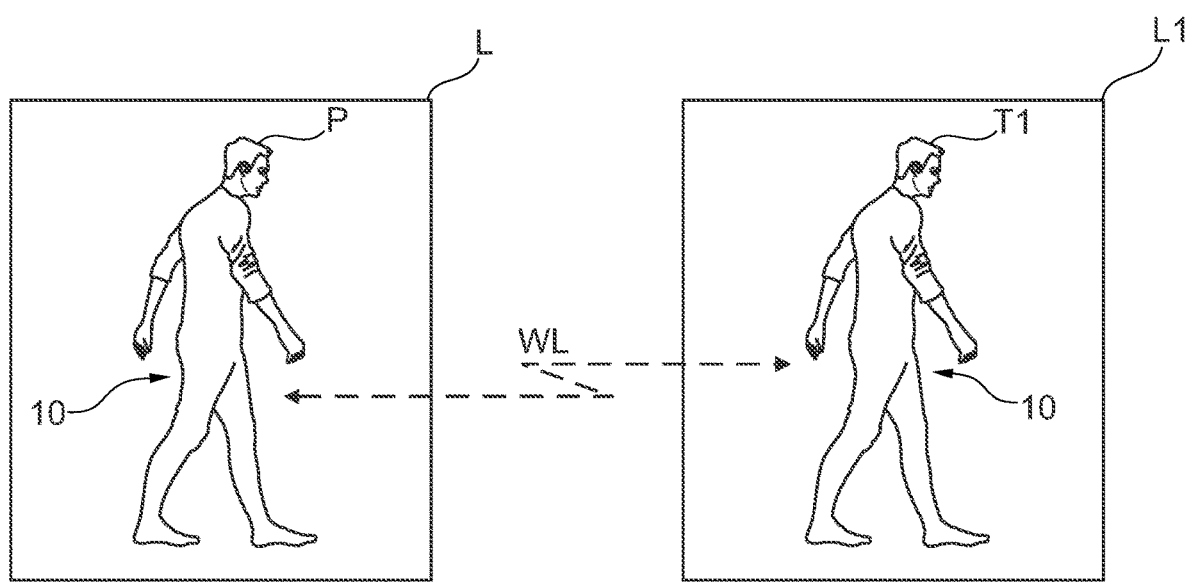
FIG. 10 a schematical view of a patient and a remote trainer according to the present invention.

FIG. 10 shows a schematical view of a patient P and a remote trainer T1 according to the present invention.

In this embodiment, a patient P is equipped with said control system 10 disclosed in FIG. 7 and located at location L.

In this embodiment, a remote trainer T1 is equipped with said control system 10 disclosed in FIG. 7 and located at location L1 remote from the location L of the patient P.

The control system 10 of a patient P and the control system 10 of a remote trainer T1 are interconnected.

The connection between the control system 10 of the remote trainer T1 and the control system 10 of the patient P is established by a wireless link WL.

By means of a wireless link WL between the control system 10 of the patient P and the control system 10 of the remote trainer T1 it is possible that control algorithms from the controller 14 of the control system 10 of the remote trainer T1 are copied to the controller 14 of the control system 10 of the patient P.

However, also copying control algorithms from the controller 14 of the control system 10 of one remote trainer T1 to the controller 14 of the control system 10 of two or more patients P located in different locations is possible.

It is also possible that the two or more patients differ in terms of progress in the rehabilitation process.

In this embodiment, the tracking and estimating is performed online and in real-time.

However, also tracking and estimating offline and with time-delay could be possible.

Not shown in FIG. 10 is that it could be generally possible, that the one or more patients P watch the remote trainer T1 and vice versa—via e.g. a standard screen, a beamer, a computer, a laptop, a tablet computer, or a mobile phone.

It could also be possible that the patient P and the remote trainer T1 communicate with each other via a general telecommunication device.

Not shown in FIG. 10 is that the controller may in general allow that tracking and estimating is performed from one patient to another patient.

Not shown in FIG. 10 is that it could be generally possible, that the one or more patients P and the remote trainer T1 communicate within an augmented and/or virtual reality module as described for the embodiment in FIG. 7.

In this regard, also gamification is possible.

Figure 11:
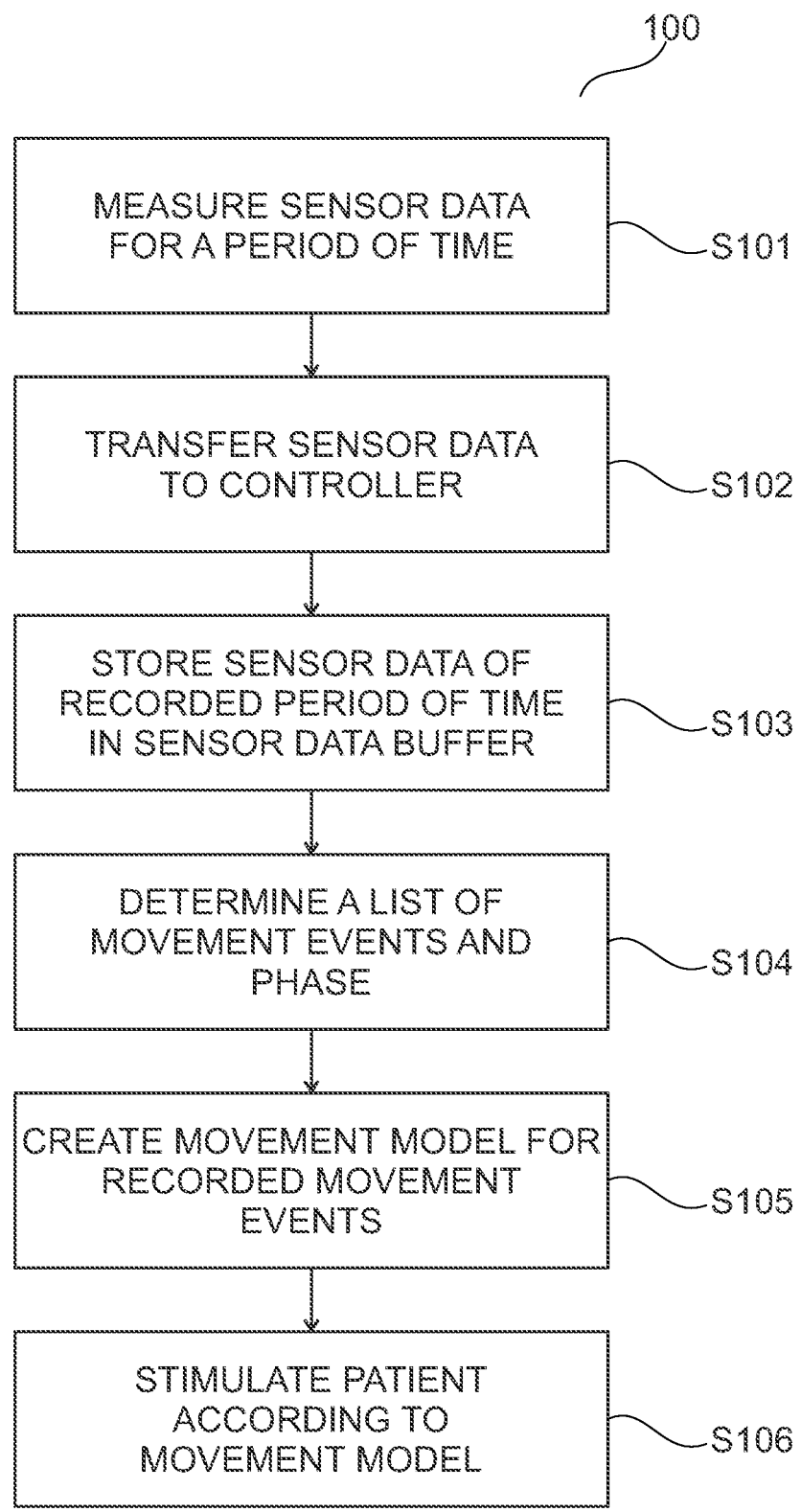
FIG. 11 a flow chart of the offline workflow a control system according to the present invention.

FIG. 11 shows a flow chart of the offline workflow of a control system for a movement reconstruction and/or restoration system for a patient according to the present invention.

It is applicable, inter alia, to all described embodiments of the invention described in this disclosure.

The offline workflow 100 for the control system 10 for a gait reconstruction and/or restoration system for a patient P as disclosed in FIG. 7 and FIG. 8A comprises the steps S101-S106.

In starting step S101 the one or more sensors 12 or the one or more sensor networks measure sensor data for a period of time of minimum one complete movement cycle.

In one embodiment, the movement cycle could be a gait cycle.

In an alternative embodiment, the movement cycle could be a swim or row cycle, or standing up, or sitting down.

In an alternative embodiment, the movement cycle could be any other movement.

In step S102 the sensor data are transferred to the controller 14.

In step S103, accumulated sensor data for the recorded period of time are stored in the sensor data buffer of the controller 14.

After that, in step S104, based on the accumulated sensor data for the recorded period of time in the sensor data buffer, the controller 14 determines a list of different movement events and phase offline.

For gait, possible gait events could include but are not limited to initial ground contact, heel strike, foot flat, loading response, midstance, terminal stance, heel off, preswing, toe off, initial swing, midswing, terminal swing, and/or heel strike (or e.g. pre-swing, swing, loading response, stance).

However, it could be possible that there are only two gait events, foot-strike and foot-off.

After the determination of a list of different movement events and phase offline in step 104, a movement model for the recorded movement events is created in step S105.

After that, in step S106 stimulation of the patient is performed.

It could be possible to use the created movement model offline at any time.

The controller 14 programs the IPG 18 to deliver the correct stimulation via the lead 20 according to the movement model determined offline by the controller 14.

According to the movement model determined offline the movement phase always takes the same value at the same event.

Performing the tracking and estimating offline may allow to use criteria that could not be used on real-time.

Note that it is possible that the sensor data buffer of the controller 14 could comprise accumulated sensor data from one patient P, and/or from two or more patients P.

However, it is also possible that the sensor buffer could comprise accumulated sensor data from one or more trainers T and/or one or more healthy subjects.

Not shown in FIG. 11 is that recorded sensor data could be preprocessed using a Kalman filter.

Figure 12:
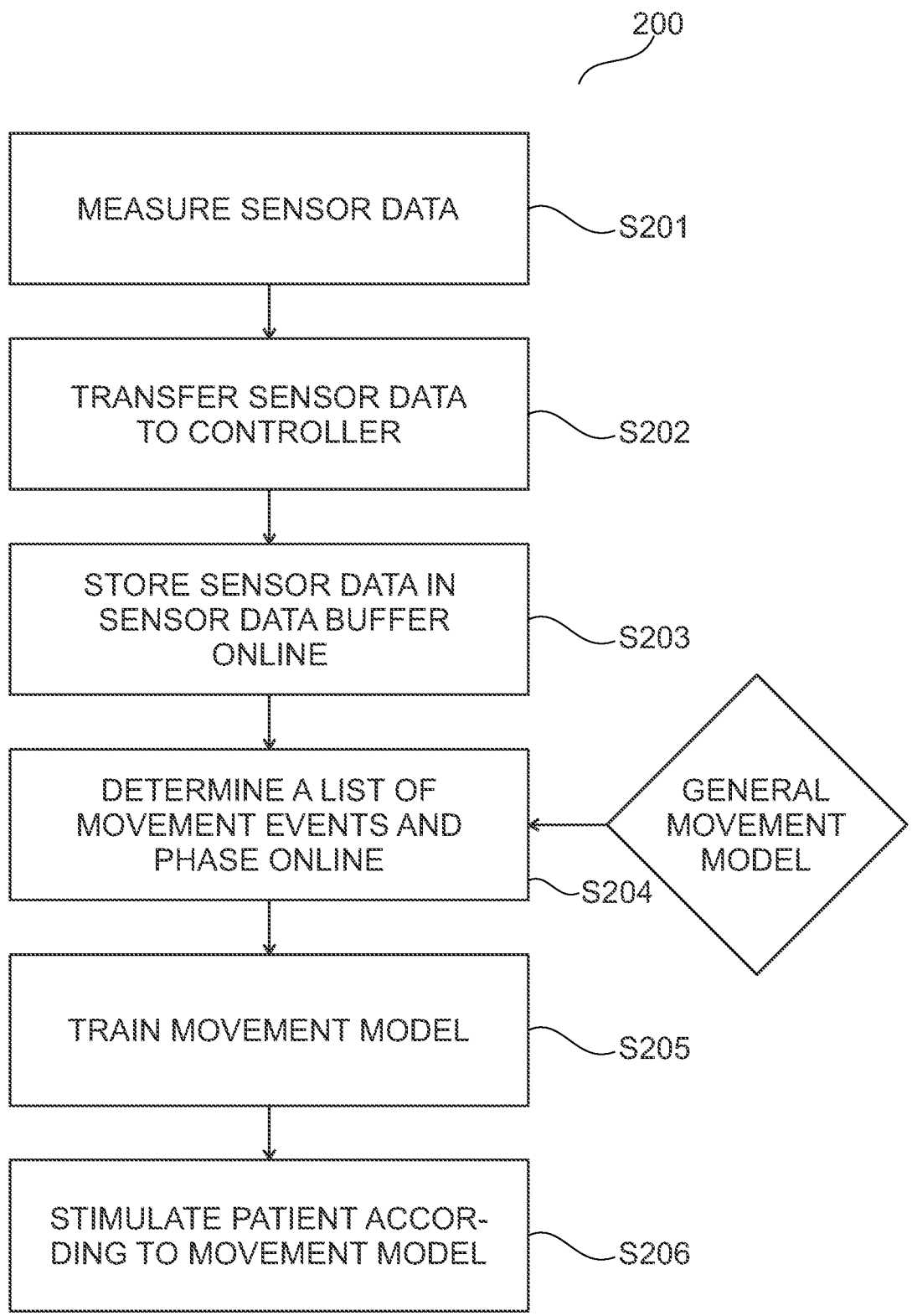
FIG. 12 a flow chart of the online workflow of a control system according to the present invention.

FIG. 12 shows a flow chart of the online workflow of a control system for a movement reconstruction and/or restoration system for a patient according to the present invention.

It is applicable, inter alia, to all described embodiments of the invention described in this disclosure.

The online workflow 200 for the control system 10 for a movement reconstruction and/or restoration system for a patient P as disclosed in FIG. 7 and FIG. 8A comprises the steps S201-S206.

In starting step S201 one or more sensors 12 or one or more sensor networks measure sensor data.

In step S202 the sensor data are transferred from the sensor 12 to the sensor data buffer of the controller 14.

In step S203 sensor data for the recorded period of time are stored online in the sensor data buffer of the controller 14.

In other words, the sensor data buffer is always updated online by recent sensor data from the sensor(s) 12.

Based on a general movement model and accumulated sensor data in the sensor data buffer of the controller 14, in step S204, the controller 14 determines a list of different movement events and phase for all recorded movement events.

For gait, possible movement events, gait events, respectively, could include but are not limited to initial ground contact, heel strike, foot flat, loading response, midstance, terminal stance, heel off, preswing, toe off, initial swing, midswing, terminal swing, and/or heel strike.

However, it could be possible that there are only two gait events, foot-strike and foot-off.

Various sensor data inputs from the sensor(s) 12 update the sensor data buffer and as soon as a whole movement, e.g. gait cycle, is detected, the past movement event, e.g. gait event, is determined online.

In step 205 the controller 14 trains the movement model using recent accumulated sensor data to adapt the particular movement of the patient P.

In step S206 stimulation of the patient P is performed according to the movement model.

The controller 14 programs the IPG 18 to deliver the correct stimulation via the lead 20 according to the recent movement model determined online by the controller 14.

The online workflow 200 realizes a real-time solution and a real-time data transfer.

Note that it is possible that the general movement model used for fusing with recent sensor data could be based on accumulated sensor data from one patient P, and/or from two or more patients P.

However, it is also possible that the general movement model used for fusing with recent sensor is based on sensor data from one or more trainers T and/or one or more healthy subjects.

It could be possible to stop the online learning process when the movement model is good enough and to store it for further sessions with the same patient P.

Not shown in FIG. 12 is that recorded sensor data could be preprocessed using a filter.

Not shown in FIG. 12 is that the filter could be a Kalman filter.

However, also other types of filters could be generally used to preprocess recorded sensor data.

Not shown in FIG. 12 is that the online workflow 200 could also be used for a control system 10 for a movement reconstruction and/or restoration system for diverse movements including e.g. walking, running, cycling, swimming, rowing, standing up, sitting down.

Figure 13:
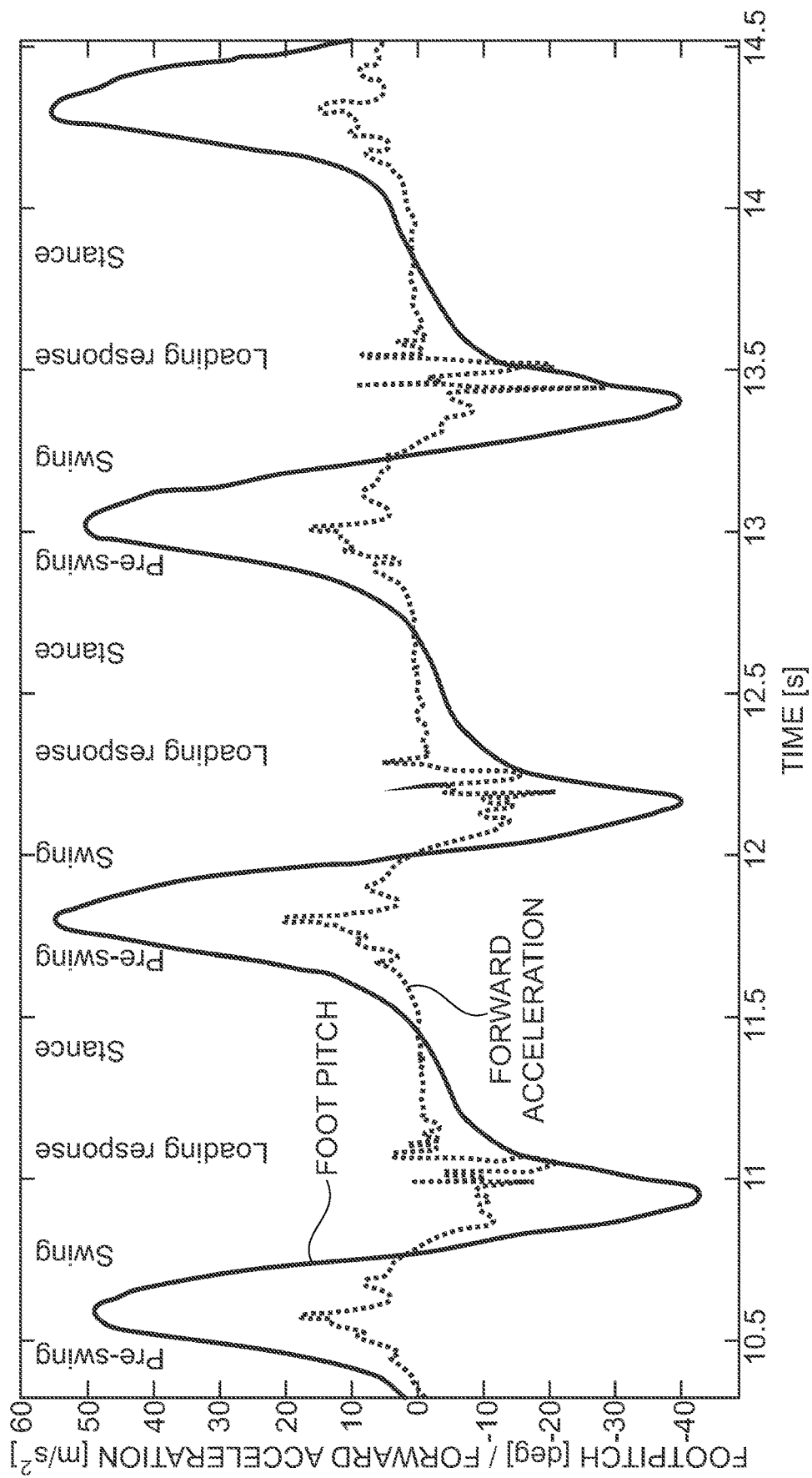
FIG. 13 a schematical diagram of food pitch/forward acceleration of a patient equipped with the control system disclosed in FIG. 7.

FIG. 13 shows a schematical diagram of foot pitch/forward acceleration of a patient P equipped with the control system disclosed in FIG. 7.

Here, the patient P is equipped with one IMU 12a per foot.

Alternatively, the patient P could be equipped with the control system 10 described in FIG. 7 including one IMU 12a and one respective sensor insole 300 for the left or the right foot.

In another embodiment, the patient P could be equipped with two or more IMUs 12a per foot.

Further, the IMU 12a and/or the sensor insole 300 can be replaced by another type of sensor 12 including but not limited to e.g. a piezo element.

In this embodiment, it could be possible that the piezo element is integrated in wearables like e.g. a sock, a knee sock, tights, a shoe.

The foot pitch (degree) and forward acceleration (meter per $s^2$) of the right foot of a patient P equipped with the control system 10 disclosed in FIG. 7 during walking is shown.

From these signals, clearly the cadence, pre-swing, swing, loading response and stance can be identified.

The same events and parameters can be identified for the left foot.

As walking is a periodic motion, all measured signals are also periodic.

By combining gait phase and cadence information of both feet of the patient P together with the gait phase and cadence of the stimulation input, a reliable gait phase and cadence estimate can be provided.

Note that gait can vary a lot between different patients P as well as for a single patient P for different walking speeds and different assistive devices (body-weight support, walker, crutches, etc.).

Especially for impaired gait, not all gait events are always present.

Hence, it is always possible to estimate the cadence by extracting the base frequency of the measured signals.

Moreover, machine-learning methods can be used to adapt the gait phase estimation to the specific gait of the patient P.

The level of agreements and discrepancies between motion of the left and right foot, and the stimulation input, can be used to give an indication of the gait phase estimation reliability, e.g., the measured cadence of the left foot should be equal to the measured cadence of the right foot and the cadence of the provided stimulation, and the left foot and right foot should be (roughly) in anti-phase.

In the control loop also use can made of the realization that the feet do not move independently from each other but are connected mechanically via the hip and on neural level via the spinal cord.

In particular, inhibitory reflex circuits in the spinal cord modulate neural firing rates (and hence modulate recruitment of motor neurons through EES).

Note that the example control and estimation routines included herein can be used with various system configurations. The control methods and routines disclosed herein may be stored as executable instructions in non-transitory memory and may be carried out by a control system 10 e.g. as a part of the controller 14 in combination with the sensors 12, the programmer 16, the stimulation system 18, the lead 20, and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of a computer readable storage medium in the controller 14, where the described actions are carried out by executing the instructions in a control system 10 including the various hardware components.

REFERENCES 10 control system
12 sensor
12a inertial measurement unit (IMU)
12b pressure sensor
12c sensor network
14 controller
16 programmer
18 implantable pulse generator (IPG)
20 lead
22 training entity 22a exoskeleton
24 electrode module
24a electrode for FES
24b electrode for EES
100 offline workflow
200 online workflow
300 sensor insole
di distal end
m movement model
pr proximal end
L location of the patient
L1 remote location of the remote trainer T1
P patient
S Shoe
T trainer/rehabilitation specialist
T1 remote trainer/remote rehabilitation specialist
CMB custom muscle blocks
COM connection, communication line
EES epidural electrical stimulation
FMB functional muscle block
WL wireless link
WSN wireless network, connection
STP space time programmer
TEL connection, telemetry line
LVLat left vastus lateralis
RVLat right vastus lateralis
Lll left iliopsoas
Rll right iliopsoas
LRF left rectus femoris
RRF right rectus femoris
LST left semitendinosus
RST right semitendinosus
LTA left tibialis anterior
RTA right tibialis anterior
LMG left medial gastrocnemius
RMG right medial gastrocnemius
LSol left soleus
RSol right soleus
LFHL left flexor hallucis longus
RFHL right flexor hallucis longus
S101 step of offline workflow
S102 step of offline workflow
S103 step of offline workflow
S104 step of offline workflow
S105 step of offline workflow
S106 step of offline workflow
S201 step of online workflow
S202 step of online workflow
S203 step of online workflow
S204 step of online workflow
S205 step of online workflow
S206 step of online workflow

The invention claimed is:

1. A control system for a movement reconstruction and/or restoration system for a patient to support the patient's own natural control loop in determining movement cadence without forcing motion, comprising:
 at least one sensor;
 at least one controller;
 at least one programmer;
 at least one stimulation system;
 wherein the controller is connected with the at least one sensor, the at least one programmer, and the at least one stimulation system;
 wherein the at least one sensor is configured to be a part of or attached to a training entity in order to:
  create and/or guide a movement model for a patient; or
  adjust stimulation settings based on sensor input;
 wherein the at least one stimulation system is configured based on measured sensor data of a minimum of one complete movement cycle of the patient, the movement has a regular and characteristic pattern for a healthy subject.

2. The control system of claim 1, wherein the training entity is a trainer and/or physiotherapist.

3. The control system of claim 1, wherein the training entity is or comprises a training apparatus, wherein the apparatus is at least one of an exoskeleton, a robot, a treadmill, a cycling machine and/or a body weight support system.

4. The control system of claim 1, wherein the controller is configured and arranged for tracking and estimating the training entity movement and for translating it into stimulation data, based on the estimated movement, being provided by the stimulation system to the patient for the patient training for movement reconstruction and/or restoration.

5. The control system of claim 4, wherein the controller is configured and arranged so that the tracking and estimating is performed online and/or offline.

6. The control system of claim 4, wherein the controller is configured and arranged that the tracking and estimating is performed online and/or in real-time and/or with time delay.

7. The control system of claim 4, wherein the controller is configured and arranged so that tracking and estimating is performed from one patient to another patient.

8. The control system of claim 1, further comprising a sensor network formed from more than one of the at least one sensor, wherein the sensor network is connected to the controller.

9. The control system of claim 1, further comprising an augmented and/or virtual reality module, which is configured and arranged to provide information related to movement reconstruction and/or restoration, especially information related to the training to be performed or being performed for movement reconstruction and/or restoration.

10. The control system of claim 9, wherein the augmented and/or virtual reality module is configured and arranged to provide gamification information related to movement reconstruction and/or restoration.

11. The control system of claim 1, wherein the at least one sensor is or comprises at least one of an inertial measurement unit (IMU), an optical sensor, a camera, a piezo element, a velocity sensor, an accelerometer, a magnetic field sensor, a torque sensor, a pressure sensor, a displacement sensor, an EMG measurement unit, a goniometer, a magnetic position sensor, a hall sensor, a gyroscope and/or motion tracking video cameras, or infra-red cameras.

12. The control system of claim 1, wherein the training entity is the patient himself or herself.

13. The control system of claim 1, wherein the control system has a pre-warning module, which is configured and arranged to provide a pre-warning signal indicative of providing an upcoming stimulation event.

14. A method for movement reconstruction, comprising:
 responsive to detection of motion by at least one sensor coupled to a training entity:
  receiving a signal from the at least one sensor at a controller, the controller coupled to a programmer;
  generating stimulation instruction by the programmer based on the signal, the signal includes measurements recorded during at least one complete movement cycle of a patient, the movement has a regular and characteristic pattern for a healthy subject;

commanding generation of stimulation pulses at the controller based on the stimulation instructions provided by the programmer;
receiving the stimulation pulses at a pulse generator;
transmitting the stimulation pulses to the patient through electrical leads connected to the pulse generator to support the patient's own natural control loop in determining movement cadence without forcing motion.

15. The method of claim 14, wherein detection of motion by at least one sensor includes attaching the at least one sensor to the patient's body and wherein the at least one sensor is included in a sensor network when more than one of the at least one sensor is connected to the controller.

16. The method of claim 14, wherein further comprising receiving data at the controller from the training entity and wherein the training entity is an entity separate from the patient and configured to define movement of the patient.

17. The method of claim 14, wherein generating stimulation instructions by the programmer includes receiving the signal from the at least one sensor at the programmer via the controller, adjusting stimulation parameters of a task based on the signal and sending the stimulation instructions to the controller through a communication link and wherein the programmer is a mobile device installed with applications.

18. The method of claim 14, wherein transmitting the stimulating pulses to the patient includes attaching the electrical leads to regions of the patient where stimulation is desired.

19. The method of claim 18, wherein the pulse generator is implanted subcutaneously in the patient and wherein transmitting the stimulation pulses to the patient provides epidural electrical stimulation.

20. The method of claim 14, further comprising updating a movement model implemented at the programmer, wherein the movement model is trained based on data generated from movement reconstruction of more than one patient.

* * * * *